US005632991A

United States Patent [19]
Gimbrone, Jr.

[11] Patent Number: 5,632,991
[45] Date of Patent: *May 27, 1997

[54] ANTIBODIES SPECIFIC FOR E-SELECTIN AND THE USES THEREOF

[75] Inventor: Michael A. Gimbrone, Jr., Jamaica Plain, Mass.

[73] Assignee: Brigham & Women's Hospital, Boston, Mass.

[*] Notice: The term of this patent shall not extend beyond the expiration date of Pat. No. 5,403,713.

[21] Appl. No.: 365,470

[22] Filed: Dec. 29, 1994

Related U.S. Application Data

[63] Continuation-in-part of Ser. No. 102,510, Aug. 5, 1993, Pat. No. 5,403,713, which is a continuation of Ser. No. 850,802, Mar. 13, 1992, abandoned, which is a division of Ser. No. 270,860, Nov. 14, 1988, abandoned.

[51] Int. Cl.$^6$ .................... A61K 39/395; A61K 39/44; C07K 16/28
[52] U.S. Cl. .................... 424/178.1; 424/143.1; 424/172.1; 530/395; 530/391.7
[58] Field of Search .................... 424/152.1, 172.1, 424/178.1, 143.1; 530/388.22, 389.1, 391.1, 391.7

[56] References Cited

U.S. PATENT DOCUMENTS

| | | | |
|---|---|---|---|
| 4,675,382 | 6/1987 | Murphy | 530/350 |
| 4,727,028 | 2/1988 | Santerre et al. | 435/240.2 |
| 4,740,470 | 4/1988 | Cohen et al. | 435/172.3 |
| 4,797,277 | 1/1989 | Arfors | 424/85.8 |
| 4,840,793 | 6/1989 | Todd, III et al. | 424/85.8 |
| 5,011,778 | 4/1991 | Newman et al. | 435/240.27 |
| 5,081,034 | 1/1992 | Bevilacqua et al. | 435/252.33 |
| 5,116,613 | 5/1992 | Haber et al. | 424/85.8 |
| 5,256,413 | 10/1993 | Haber et al. | 424/85.8 |
| 5,403,713 | 4/1995 | Bevilacqua et al. | 435/7.1 |

OTHER PUBLICATIONS

Aruffo, A. and Seed, B., "Molecular cloning of a CD28 cDNA by a high efficiency COS cell expression system," *PNAS USA* 84:8573–8577 (1987).

Baggiolini et al., "Neutrophil-activating Peptide-1/Interleukin 8, a Novel Cytokine That Activates Neutrophils," *J. Clin. Invest.* 84:1045–1049 (1989).

Bar-Shavit et al., "Monocyte Chemotaxis: Stimulation by Specific Exosite Region in Thrombin," *Science* 220:278–731 (1983).

Benjamin et al., "A Blocking Monoclonal Antibody to Endothelial-Leukocyte Adhesion Molecule-1 (ELAM1)," *Biochem. Biophys. Res. Comm.* 171(1):348–353 (1990).

Bevilacqua, M.P. and Gimbrone, M.A., "Inducible Endothelial Functions in Inflammation and Coagulation," *Seminars in Thrombosis and Hemostasis* 13(4):425–433 (1987).

Bevilacqua, M.P. and Nelson, R.M., "Selectins," *J. Clin. Invest.* 91:379–387 (1993).

Bevilacqua et al., "Endothelial-Dependent Mechanisms of Leukocyte Adhesion: Regulation by Interleukin-1 and Tumor Necrosis Factor," *Leukocyte Immigration and Its Sequelae, Satellite Symp. of the 6th Intl. Cong. of Immunol.*, Henry Z. Movat, ed., S. Karger, Basel, pp. 79–93 (1987).

Bevilacqua et al., "Endothelial Leukocyte Adhesion Molecule 1: An Inducible Receptor for Neutrophils Related to Complement Regulatory Proteins and Lectins," *Science* 243:1160–1165 (1989).

Bevilacqua et al., "Endothelial–Leukocyte Adhesion: Stimulation of Endothelial Dependent Mechanisms by Monokines," *4th Intl. Symp. Biol. Vasc. Endothelial Cell*:13 Abstract (1986).

Bevilacqua et al., "Identification of an inducible endothelial-leukocyte adhesion molecule," *PNAS USA* 84:9238–9242 (1987).

Bevilacqua et al., "Identification of an Inducible Endothelial-Leukocyte Adhesion Molecule (E–LAM 1) Using Monoclonal Antibodies (Mab)," *Fed. Proc.* 46:405 Abstract No. 514 (1987).

Bevilacqua et al., "Interleukin 1 Acts on cultured Human Vascular Endothelium to Increase the Adhesion of Polymorphonuclear Leukocytes, Monocytes, and Related Leukocyte Cell Lines," *J. Clin. Invest.* 76:2003–2011 (1985).

Bevilacqua et al., "Interleukin 1 (IL–1) Induces Biosynthesis and Cell Surface Expression of Procoagulant Activity in Human Vascular Endothelial Cells," *J. Exp. Med.* 160:618–623 (1984).

Bevilacqua et al., "Interleukin–1 Activation of Vascular Endothelium," *Am. J. Path.* 121:392–403 (1985).

Bevilacqua et al., "Regulation of the Fibrinolytic System of Cultured Human Vascular Endothelium by Interleukin 1," *J. Clin. Invest.* 78:587–591 (1992).

Bevilacqua et al., "Selectins: A Family of Adhesion Receptors," *Cell* 67:233 (1991).

Bode et al., "Fibrin–Targeted Recombinant Hirudin Inhibits Fibrin Deposition on Experimental Clots More Efficiently Than Recombinant Hirudin," *Circulation* 90:1956–1963 (1994).

(List continued on next page.)

*Primary Examiner*—Thomas M. Cunningham
*Attorney, Agent, or Firm*—Sterne, Kessler, Goldstein & Fox, PLLC

[57] ABSTRACT

A method is provided for selectively targeting a therapeutic agent to a site of activated endothelium by administering a pharmaceutical composition comprising a therapeutically effective amount of an E-selectin (formerly called ELAM-1) specific monoclonal antibody conjugated to a therapeutic agent. An immunoconjugate comprising an E-selectin specific monoclonal antibody and a therapeutic agent is also provided. A method is also provided for the treatment of a vascular smooth muscle cell proliferative disorder, vasculitis, inflammation, post-reperfusion injury, microbial infections, acute or chronic allograft rejection, and leukemia, as well as for the inhibition of metastatic spread of tumor cells, by administering a pharmaceutical composition comprising a therapeutically effective amount of an E-selectin antibody, or antibody fragment, either alone, or conjugated to a therapeutic agent.

15 Claims, 13 Drawing Sheets

OTHER PUBLICATIONS

Briscoe et al., "Predictive Value of Inducible Endothelial Cell Adhesion Molecule Expression for Acute Rejection of Human Cardiac Allografts," *Transplantation* 59(2) :204–211 (1995).

Brockmeyer et al., "Distribution of Cell Adhesion Molecules (ICAM-1, VCAM-1, ELAM-1) in Renal Tissue During Allograft Rejection," *Transplantation* 55(3):610–615 (1993).

Cavender et al., "Interleukin 1 Increases the binding of Human B and T Lymphocytes to Endothelial Cell Monolayers," *J. Immunol.* 136(1):203–207 (1986).

Chang, P. and Aronson, D.L., "A Microtiter Plate Reader Assay for Factor VIII," *Thrombosis Research* 66:599–602 (1992).

Collins et al., "Structure and Chromosomal Location of the Gene for Endothelial–Leukocyte Adhesion Molecule 1," *J.Biol. Chem.* 266(4):2466–2473 (1991).

Collins et al., "Von Willebrand Factor Release and P–Selectin Expression is Stimulated by Thrombin and Trypsin but not IL–1 in Cultured Human Endothelial Cells," *Thromb. Haemostasis* 70(2):346–350 (1993).

Cotran et al., "Endothelial Activation During Interleukin 2 Immunotherapy," *J. Immunol.* 139(12):1883–1888 (1987).

Cotran et al., "Induction and Detection of a Human Endothelial Activation Antigen In Vivo," *J. Exp. Med.* 164:661–666 (1986).

Cybulsky, M.I. and Gimbrone, M.A., "Endothelial Expression of a Mononuclear Leukocyte Adhesion Molecule During Atherogenesis," *Science* 251:788–791 (1991).

Daniel et al., "Thrombin Stimulates c–sis Gene Expression in Microvascular Endothelial Cells," *J.Biol. Chem.* 261(21):9579–9582 (1986).

Darnell et al., in: Molecular Cell Biology, Scientific American Books, Inc., p. 662 (1986).

Davey, M.G. and Lüscher, E.F., "Actions of Thrombin and Other Coagulent and Proteolytic Enzymes on Blood Platelets," *Nature* 216:857–858 (1967).

Dewerchin et al., "Effect of Chemical Conjugation of Recombinant Single–Chain Urukinase–Type Plasminogen Activator With Monoclonal Antiplatelet Antibodies on Platelet Aggregation and on Plasma Clot Lysis In Vitro and In Vivo," *Blood* 78(4):1005–1018 (1991).

Drake et al., "Expression of Tissue Factor, Thrombomodulin, and E-Selectin in Baboons with Lethal *Escherichia coli* Sepsis," *Amer. J. Pathol.* 142(5):1458–1470 (1993).

Dunn, C.J. and Fleming, W.E., "The Role of Interleukin–1 in the Inflammatory Response with Particular Reference to Endothelial Cell–Leukocyte Adhesion," in: The Physiologic, Metabolic and Immunologic Actions of Interleukin–1, Kluger et al., eds., Liss, N.Y., pp. 45–54 (1985).

Dustin et al., "Induction by IL 1 and Interferon–γ: Tissue Distribution, Biochemistry, and Function of a Natural Adherence Molecule (ICAM01)," *J. Immunol.* 137(1):245–254 (1986).

Fuggle et al., "Variation in Expression of Endothelial Adhesion Molecules in Pretransplant and Transplanted Kidneys—Correlation with Intragraft Events," *Transplantation* 55(1) :117–123 (1993).

Gamble et al., "Stimulation of the adherence of neutrophils to umbilical vein endothelium by human recombinant tumor necrosis factor," *PNAS USA* 82:8667–8671 (1985).

Garcia et al., "Thrombin–Induced Increase in Albumin Permeability Across the Endothelium," *J. Cell. Physiol.* 128:96–104 (1986).

Gimbrone, M.A., "Vascular Endothelium: Nature's Blood–Compatible Container," *Ann. N.Y. Acad. Sci.* 516:5–11 (1987).

Gimbrone et al., "Endothelial–dependent Mechanisms of Leukocyte Adhesion: Role of Monokines," *Thromb. Hemostas.* 58:325 Abstract No. 1184 (1987).

Graham, D.J. and Alexander, J.J, "The effects of thrombin on bovine aortic endothelial and smooth muscle cells," *J. Vasc. Surg.* 11:307–313 (1990).

Gundel et al., "Endothelial Leukocyte Adhesion Molecule–1 Mediates Antigen–induced Acute Airway Inflammation and Late-phase Airway Obstruction in Monkeys," *J. Clin. Invest.* 88:1407–1411 (1991).

Haber et al., "Innovative Approaches to Plasminogen Activator Therapy," *Science* 243:51–56 (1989).

Harker, L.A., "Strategies for inhibiting the effects of thrombin," *Blood Coagulation and Fibrinolysis* 5(1) :S47–S58 (1994).

Harlan, J.M., "Leukocyte–Endothelial Interactions," *Blood* 65(3):513–525 (1985).

Harlan et al., "α–Thrombin Induces Release of Platelet–derived Growth Factor–like Molecule(s) by Cultured Human Endothelial Cells,"*J. Cell Biol.* 103:1129–1133 (1986).

Hession et al., "Endothelial leukocyte adhesion molecule 1: Direct expression cloning and functional interactions," *PNAS USA* 87:1673–1677 (1990).

Huang, A.J. and Silverstein, S.C., "Mechanisms of Neutrophil Migration across Endothelium," in: Endothelial Cell Dysfunctions, Simionescu and Simionescu, eds., Plenum Press, N.Y., pp. 201–231 (1992).

Jaffe et al., "Correlation between Thrombin–induced Prostacylin Production and Inositol Triphosphate and Cytosolic Free Calcium Levels in Cultured Human Endothelial Cells," *J. Biol. Chem.* 262(18):8557–8565 (1987).

Jalkanen et al., "Lymphocyte Recognition of High Endothelium: Antibodies to Distinct Epitopes of an 85–95–kD Glycoprotein Antigen Differentially Inhibit Lymphocyte Binding to Lymph Node, Mucosal, or Synovial Endothelial Cells," *J. Cell Biol.* 105:983–990 (1987).

Kishimoto et al., "Antibodies Against Human Neutrophil LECAM–1 (LAM–1/Leu–8/DREG–56 antigen) and Endothelial Cell ELAM–1 Inhibit a Common CD18–Independent Adhesion Pathway In Vitro," *Blood* 78(3):805–811 (1991).

Kishimoto et al. "Neutrophil Mac–1 and MEL–14 Adhesion Proteins Inversely Regulated by Chemotactic Factors," *Science* 245:1238–1241 (1989).

Kollonitsch, J. and Barash, L., "Organofluorine Synthesis via Photofluorination: 3–Fluoro–D–alanine and 2–Deuterio Analogue, Antibacterials Related to the Bacterial Cell Wall," *J. Amer. Chem. Soc.* 98(18):5591–5593 (1976).

Lasky et al., "Cloning of a Lymphocyte Homing Receptor Reveals a Lectin Domain," *Cell* 56:1045–1055 (1989).

Lefkovits, J. and Topol, E.J., "Direct Thrombin Inhibitors in Cardiovascular Medicine," *Circulation* 90(3):1522–1536 (1994).

Lo et al., "Interaction of ELAM–1 and its Ligand Sialyl–Lewis X Activates CD11/CD18 to Mediate Leukocyte Adhesion," *FASEB J.* 5:A1602 Abstract No. 7149 (1991).

Lo et al., "Transient Adhesion of Neutrophils to Endothelium," *J. Exp. Med.* 169:1779–1793 (1989).

Luscinskas et al., "Cytokine–Activated Human Endothelial Monolayers Suppprt Enhanced Neutrophil Transmigration via a Mechanism Involving Both Endothelial–Leukocyte Adhesion Molecule–1 and Intercellular Adhesion Molecule–1," *J. Immunol.* 146(5):1617–1625 (1991).

Means, G.E. and Feeney, R.E., in: Chemical Modification of Proteins, Holden–Day, pp. 39–43 (1974).

Mentzer et al., "Adhesion of T Lymphocytes to Human Endothelial Cells is Regulated by the LFA–1 Membrane Molecule," *J. Cells. Physiol.* 126:285–290 (1986).

Mentzer et al., "Alpha and Beta Subunits of the LFA–1 Membrane Molecule Are Involved in Human Monocyte–Endothelial Cell Adhesion," *J. Cell. Physiol.* 130:410–415 (1987).

Mulligan et al., "Role of Endothelial–Leukocyte Adhesion Molecule 1 (ELAM–1) in Neutrophil–mediated Lung Injury in Rats," *J. Clin. Invest.* 88:1396–1406 (1991).

Nelken et al., "Thrombin Receptor Expression in Normal and Atherosclerotic Human Arteries," *J. Clin. Invest.* 90:1614–1621 (1992).

Nemerson, Y., "Tissue Factor and Hemostasis," *Blood* 71(1):1–8 (1988).

Okayama, H. and Berg, P., "A cDNA Cloning Vector That Permits Expresion of cDNA Inserts in Mammalian Cells," *Mol. Cell Biol.* 3(2):280–289 (1983).

Phillips et al., "ELAM–1 Mediates Cell Adhesion by Recognition of a Carbohydrate Ligand, Sialyl–Le$^x$," *Science* 250:1130–1132 (1990).

Picker et al., "ELAM–1 is an adhesion molecule for skin–homing T cells," *Nature* 349:796–799 (1991).

Pober et al., "Effects of tumour necrosis factor and related cytokines on vascular endothelial cells," *Ciba Found. Symp.* 131:170–184 (1987).

Pober et al., "Overlapping Patterns of Activation of Human Endothelial Cells by Interleukin 1, Tumor Necrosis Factor, and Immune Interferon," *J. Immunol.* 137(6):1893–1896 (1986).

Pober et al., "Two Distinct Monokines, Interleukin 1 and Tumor Necrosis Factor, Each Independently Induce Biosynthesis and Transient Expression of the same Antigen on the Surface of Cultured Human Vascular Endothelial Cells," *J. Immunol.* 136(5):1680–1687 (1986).

Pohlman et al., "An Endothelial Cell Surface Factor(s) Induced In vitro by Lipopolysaccharide, Interleukin 1, and Tumor Necrosis Factor–$\alpha$ Increases Neutrophil Adherence by a CDw18–Dependent Mechanism," *J. Immunol.* 136(12):4548–4553 (1986).

Polte et al., "cDNA for endothelial Leukocyte adhesion molecule 1 (ELAM1): sequence differences," *Nucleic Acids Res.* 18(4):1083 (1989).

Rade et al., "Viral Vector–Mediated Expression of Biologically Active Hirudin in Cultured Endothelial Cells," *Circulation* 88(4):I–418 Abstract No. 2244 (1993).

Rapaport, S.I., "The Initiation of the Tissue Factor Dependent Pathway of Blood Coagulation," *Adv. Exp. Med. Biol.* 281:97–103 (1990).

Rothlein et al., "A Human Intercellular Adhesion Molecule (ICAM–1) Distinct From LFA–1," *J. Immunol.* 137(4):1270–1274 (1986).

Rydel et al., "The Structure of a Complex of Recombinant Hirudin and Human $\alpha$–Thrombin," *Science* 249:277–280 (1990).

Sago, H. and Iinuma, K., "Cell Shape Change and Cytosolic $Ca^{2+}$ in Human Umbilical–Vein Endothelial Cells Stimulated with Thrombin," *Thromb. Haemostasis* 67(3):331–334 (1992).

Schleimer, R.P. and Rutledge, B.K., "Cultured Human Vascular Endothelial Cells Acquire Adhesiveness for Neutrophils After Stimulation with Interleukin 1, Endotoxin, and Tumor–Promoting Phorbol Diesters," *J. Immunol.* 136(2):649–654 (1986).

Schlossman et al., "CD Antigens 1993," *Blood* 83(4):879–880 (1994).

Seed, B. and Aruffo, A., "Molecular cloning of the CD2 antigen, the T–cell erythrocyte receptor, by a rapid immunoselectin procedure," *PNAS USA* 84:3365–3369 (1987).

Simpson et al., "Sustained Limitation of Myocardial Reperfusion Injury by a Monoclonal Antibody that Inhibits Leukocyte Adhesion," *FASEB J.* 2(5):A1237 Abstract No. 5470 (1988).

Soper et al., "Inactivation of Bacterial D–Amino Acid Transaminase by $\beta$–Chloro–D–alanine," *J. Biol. Chem.* 252(10):3170–3175 (1977).

Sporn et al., "Inducible Secretion of Large, Biologically Potent von Willebrand Factor Multimers," *Cell* 46:185–190 (1986).

Stone, S.R. and Maraganore, J.M., "Hirudin Interactions with Thrombin," in: Thrombin: Structure and Function, Berliner, L.J., Ed., Plenum Press, N.Y., pp. 219–256 (1992).

Taylor et al., "Induction of Vascular Adhesion Molecules During Rejection of Human Cardiac Allografts," *Transplantation* 54(3):451–457 (1992).

Tedder et al., "Isolation and Chromosomal Localization of cDNAs Encoding a Novel Human Lymphocyte Cell Surface Molecule, LAM–1," *J.Exp. Med.* 170:123–133 (1989).

Thurston, G. and Turner, D., "Thrombin–Induced Increase of F–Actin in Human Umbilical Vein Endothelial Cells," *Microvascular Research* 47:1–20 (1994).

Tiemeyer et al., "Carbohydrate ligands for endothelial–leukocyte adhesion molecule 1," *PNAS USA* 88:1138–1142 (1991).

Walz et al., "Recognition by ELAM–1 of the Sialyl–Le$^x$ Determinant on Myloid and Tumor Cells," *Science* 250:1132–1135 (1990).

Wang, E. and Walsh, C., "Suicide Substrates for the Alanine Racemase of *Escherichia coli* B," *Biochemistry* 17(7):1313–1321 (1978).

Weisman et al., "Soluble Human Complement Receptor Type 1: In Vivo Inhibitor of Complement Suppressing Post–Ischemic Myocardial Inflammation and Necrosis," *Science* 249:146–151 (1990).

Yu et al., "Effects of Bacterial Lipopolysaccharide on the Binding of Lymphocytes to Endothelial Cell Monolayers," *J. Immunol.* 136(2):569–573 (1986).

Zimmerman et al., "Thrombin Stimulates Neutrophil Adherence by an Endothelial Cell–Dependent Mechanism: Characterization of the Response," *Ann. N.Y. Acad. Sci.* 485:349–368 (1986).

ANTIBODIES SPECIFIC FOR E-SELECTIN AND THE USES THEREOF

STATEMENT AS TO RIGHTS TO INVENTIONS MADE UNDER FEDERALLY-SPONSORED RESEARCH AND DEVELOPMENT

The U.S. Government has a paid-up license in this invention and the right in limited circumstances to require the patent owner to license others on reasonable terms as provided for by the terms of grant numbers P01-HL-36028 and P01-HL-48743 awarded by the National Institutes of Health.

CROSS-REFERENCES TO RELATED APPLICATIONS

This application is a continuation-in-part of U.S. patent application Ser. No. 08/102,510, filed Aug. 5, 1993, now U.S. Pat. No. 5,403,713, which was a continuation of U.S. patent application Ser. No. 07/850,802, filed Mar. 13, 1992, abandoned, which was a divisional of U.S. patent application Ser. No. 07/210,860, filed Nov. 14, 1988, abandoned. The content of all the aforesaid applications are relied upon and incorporated by reference in their entirety.

BACKGROUND OF THE INVENTION

1. Field of the Invention

The present invention relates to immunology and cellular adhesion. In particular, the invention relates to antibodies specific for endothelial leukocyte adhesion molecule-1 (formerly known as ELAM-1), which is now referred to as E-selectin (CD62E) (Schlossman et al., *Blood* 83:879-880 (1994); Bevilacqua and Nelson, *J. Clin. Invest.* 91:379-387 (1993); Bevilacqua et al., *Cell* 67:233 (1991)). More particularly, the invention relates to the use of E-selectin specific antibodies, both alone, and conjugated to a therapeutic agent, for the treatment of various disease states.

DESCRIPTION OF RELATED ART

Focal adhesion of leukocytes to the endothelial lining of blood vessels is a characteristic step in intimation and in certain vascular disease processes. Although it has long been suspected that alterations in the vessel wall could promote leukocyte adhesion (Cohnheim, J., *Lectures in General Pathology* (New Syndenham Society, London) Vol. 1, 2nd Ed. (1898)), until recently, potential mechanisms and modulators of this interaction have remained undefined (Harlan, J. M., *Blood* 65:513-525 (1985)). Certain inflammatory/immune cytokines including interleukin-1 (IL-1) and tumor necrosis factor (TNF), as well as bacterial endotoxin, have been shown to act directly on cultured human vascular endothelium to increase the adhesiveness of its surface for blood leukocytes and related cell lines (Bevilacqua et al., *J. Clin. Invest.* 76:2003-2011 (1985); Bevilacqua et al., *Am. J. Pathol.* 121:393-403 (1985); Bevilacqua et al., *Leukocyte Emigration and Its Sequelae*, Movat, H. Z., ed., Karger, N.Y. (1987), pp. 79-93; Gamble et at., *Proc. Natl. Acad. Sci. (USA)* 82:8667-8671 (1985); Schleimer et al., *J. Immunol.* 136:649-654 (1986); Dunn et al., *The Physiologic, Metabolic and Immunologic Actions of Interleukin-1*, Kluger et al., eds., Liss, N.Y. (1985), pp. 45-54; Cavender et al., *J. Immunol.* 136:203-207 (1986); Yu et al., *J. Immunol.* 136:571 (1986); and Pohlman et at., *J. Immunol.* 136:4548-4553 (1986)).

A number of leukocyte and endothelial cell surface proteins participate in endothelial cell-leukocyte adhesion. One example, ICAM-1, is expressed on a variety of hemopoietic cells and non-hemopoietic cells including vascular endothelium. ICAM-1 is a 90 kD glycoprotein which is induced by certain cytokines on endothelial cells. ICAM-1 expression is protein and mRNA synthesis-dependent and its induction is reversible (Dustin et al., *J. Immunol.* 137:245-254 (1986); Rothlein et al., *J. Immunol.* 137:1270-1274 (1986); and Pober et al., *J. Immunol.* 136:1680-1687 (1986)).

A leukocyte cell surface glycoprotein, LFA-1, is expressed on lymphocytes, granulocytes, monocytes, phagocytes and B cells. LFA-1 also plays a role in leukocyte-endothelial cell adhesion. LFA-1 is a dimeric molecule with a 177 kD (alpha or heavy) subunit and a 95 kD (beta or light) subunit. An F(ab')2 Mab has been developed to the alpha and beta subunits which effectively inhibits leukocyte adhesion to endothelial cells. Mentzer et al., *J. Cell. Physiol.* 126:285-290 (1986); Mentzer et al., *J. Cell. Physiol.* 130:410-415 (1987); Pohlman et al., *J. Immunol.* 136:4548-4553 (1986).

E-selectin is another endothelial cell surface glycoprotein that participates in endothelial-leukocyte adhesion. Upon activation by certain inflammatory cytokines such as interleukin-1 (IL-1), tumor necrosis factor (TNF) or gram-negative bacterial endotoxin (lipopolysaccharide) (LPS), E-selectin is abundantly expressed on the cell surface of endothelial cells, with a similar temporal pattern of induction as tissue factor (Pober et al., *J. Immunol.* 136:1680-1687 (1986)). E-selectin is identified by specific binding of murine monoclonal antibodies (Mab) H4/18 and H18/7, developed against stimulated endothelial cells. The time sequence of induction of the antigen recognized by H4/18 and H18/7 binding antigens and the susceptibility of its expression to metabolic inhibitors were similar to those observed for leukocyte adhesion (Bevilacqua et al., *4th Int'l Symp. Biol. Vasc. Endothelial Cell:* 13 (Abstr) (1986); Pober et al., supra; Bevilacqua et al., *Proc. Natl. Acad. Sci. (USA)* 84:9238-9242 (1987); Bevilacqua et al., in *Leukocyte Immigration and Its Sequelae, Satellite Symp.*, Henry Z. Movat, ed., S. Karger, Basil, Switzerland (1987), pp. 79-93). These putative endothelial cell surface structures were termed "endothelial-leukocyte adhesion molecules" (ELAMs), and are now termed E-selectins. Expression of E-selectin by stimulated endothelial cells was blocked by protein and RNA synthesis inhibitors, but not by cyclooxygenase inhibitors.

The H4/18 Mab immunoprecipitated two biosynthetically labeled polypeptides with molecular weights of 100 kD and 120 kD. H4/18 and F(ab')2 fragments were found to partially inhibit HL-60 cell (premyelocytic cell line) adhesion to activated HEC, but did not affect the adhesion of normal blood cells. In contrast, Mab H18/7 did block the adhesion of normal blood PMN and therefore allowed the designation of E-selectin (Bevilacqua et al., *Proc. Natl. Acad. Sci. (USA)* 84:9238-9242 (1987)).

Induction of expression of E-selectin on endothelial cells at the site of inflammation has been detected at the site of inflammation using the Mab H4/18 in microvascular endothelium of human skin (Cotran et al., *J. Exp. Med.* 164:661-666 (1986)).

The vascular endothelial lining is a biologically active interface at which multiple effector molecules involved in inflammation, thrombosis, and atherogenesis interact as components of various pathophysiologic balances (Gimbrone, M. A., *Ann. N.Y. Acad. Sci.* 516:5-11 (1987); Gimbrone, M. A., "Vascular endothelium in health and disease," in *Molecular Cardiovascular Medicine*, Haber, E., ed., Scientific American Medicine, New York (1995) pp. 49–61. Activation of endothelial cells by cytokines, such as IL-1 and TNF, and bacterial products, such as gram-negative endotoxins, typically results in a shift in the setpoint of these balances to a proinflammatory, prothrombotic state. Id.

Thrombin, via its actions as both a humoral protease and cellular agonist, is a key mediator in many of these activation-dependent processes (Coughlin et al., *J. Clin. Invest.* 78:587–591 (1992); Harker, L. A., *Blood Coagulation and Fibrinolysis* 5:S47–S58 (1994)). In addition to enzymatically converting fibrinogen to fibrin in clot formation, thrombin is a pluripotent effector molecule for endothelial cells, acting via a high affinity membrane receptor (Coughlin et al., *J. Clin. Invest.* 78:587–591 (1992)). Known effects of thrombin on cultured endothelial cells include the modulation of expression of various growth factors, as well as the generation of lipid mediators such as platelet-activating factor and prostacyclin (Daniel et al., *J. Biol. Chem.* 261:9579–9582 (1986); Zimmerman et al., *Ann. N.Y. Acad. Sci.* 485:349–368 (1986); Jaffe et at., *J. Biol. Chem.* 262:8557–8565 (1987)).

Thrombin also induces degranulation of Weibel-Palade bodies leading to secretion of the platelet adhesive protein von Willebrand factor and transient surface expression of P-selectin, an endothelial-leukocyte adhesion molecule (Sporn et al., *Cell* 46:185–190 (1986); Collins et al., *Thrombosis and Haemostasis* 70:346–350 (1993)). In an in vitro monolayer model, thrombin induces endothelial shape changes, and enhances macromolecular permeability in association with alterations in the endothelial actin cytoskeleton (Sago et at., *Thrombosis and Haemostasis* 67:331–334 (1992); Garcia et al., *J. Cell. Physiol.* 128:96–104 (1986); Thurston et al., *Microvascular Research* 47:1–20 (1994)).

In addition to these endothelial-directed actions, thrombin also stimulates platelets and leukocytes, acting as a secretogogue and chemoattractant (Davey and Luscher, *Nature* 216:857–858 (1967); Bar-Shavit et al., *Science* 220:728–731 (1983)). In view of these various actions, thrombin generation at the vessel wall-blood interface, in vivo, is predicted to be an important component of the pathophysiology of "response-to-injury" processes, such as acute and chronic inflammation, wound-healing, arterial intimal hyperplasia, and atherogenesis.

Therefore, factors determining the effective concentration of thrombin in the vicinity of the luminal surface of the endothelium may have important pathophysiologic relevance. These factors include: thrombin generation by the membrane-associated prothrombinases of activated endothelial cells, leukocytes, and platelets; hemodynamic conditions influencing boundary layer diffusion and convection; and neutralizing mechanisms, such as thrombomodulin and heparin-like glycosaminoglycans, that act to reduce thrombin activity at the endothelial-blood interface. Given the localized nature of these activation-dependent processes, and their potential for sequestration in so-called "black-holes" (Huang and Silverstein, "Mechanisms of neutrophil migration across endothelium," in *Endothelial Cell Dysfunctions*, Simionescu and Simionescu, eds., Plenum Press, New York (1992), pp. 201–231) at points of cell-cell or cell-matrix contact, a need exists for a therapeutic agent that can be selectively targeted to such sites. In addition, since multiple cell types in the circulating blood (e.g., leukocytes, platelets) and within the vessel wall (e.g., endothelium, smooth muscle cell) express receptors for thrombin (Coughlin et al., *J. Clin. Invest.* 78:587–591 (1992); Nelken et al., *J. Clin. Invest.* 90:1614–1621 (1992)), cell-selective targeting would also provide a therapeutic selectivity not currently attainable.

The immunotargeting of activators of the fibrinolytic system to the fibrin and platelet components of a developing thrombus to limit its clinical impact has been explored using monoclonal antibodies specific for fibrin or platelets. (See Haber et al., *Science* 243:52–54 (1989); U.S. Pat. No. 5,256,413, issued Oct. 26, 1993 to Haber and Matsueda; U.S. Pat. No. 5,116,613, issued May 26, 1992 to Haber and Matsueda; Dewerchin et al., *Blood* 78:1005–1018 (1991)). It has also been shown that hirudin immunoconjugates that selectively target fibrin significantly reduce fibrin deposition on the surface of experimental clots (Bode et al., *Circulation* 90:1956–1963 (1994)). Rade et al. (*Circulation* 88:1–418 (1993)) have recently published a preliminary report on viral vector-mediated transduction of cultured bovine aortic endothelial cells with a hybrid gene encoding a secretable form of hirudin.

Nonetheless, there exists a need in the art for a therapeutic method of treating disease states where endothelial activation plays a role that is based on the activation-dependent and selective immunotargeting of a therapeutic agent, such as an anti-thrombotic agent, to activated vascular endothelium.

SUMMARY OF THE INVENTION

The present invention meets this need in the art by providing a method of selectively targeting a therapeutic agent to a site of activated endothelium by administering to a patient a pharmaceutical composition containing a therapeutically effective amount of an E-selectin specific monoclonal antibody, or antibody fragment, conjugated to a therapeutic agent, and a pharmaceutically acceptable carrier.

The invention also provides a preferred embodiment of the above, wherein the monoclonal antibody is H18/7 or H4/18 and the therapeutic agent is an anti-thrombotic agent, thrombolytic agent, anti-inflammatory agent, antioxidant, anti-tumor agent, anti-smooth muscle cell proliferative agent, anti-complement agent, immunosuppressive agent, or anti-microbial agent.

The invention also provides an immunoconjugate for selectively targeting a therapeutic agent to a site of activated endothelium in a patient, comprising a monoclonal E-selectin specific antibody, or fragment thereof, and a therapeutic agent that is an anti-thrombotic agent, thrombolytic agent, anti-inflammatory agent, antioxidant, anti-tumor agent, anti-smooth muscle cell proliferative agent, anti-complement agent, immunosuppressive agent, or anti-microbial agent.

The invention also provides particularly preferred embodiments of the foregoing method and immunoconjugate, wherein the monoclonal antibody is H18/7 and the anti-thrombotic agent is hirudin.

The invention also provides a method for the treatment of inflammation by administering to a patient a pharmaceutical composition containing a therapeutically effective amount of an E-selectin specific monoclonal antibody, or antibody fragment thereof, and a pharmaceutically acceptable carrier.

The invention also provides a method for the treatment of inflammation, wherein an E-selectin specific monoclonal antibody is conjugated to an anti-inflammatory agent.

The invention also provides a method for the treatment of a microbial infection (e.g., bacterial, viral or parasitic), by administering to a patient a pharmaceutical composition containing a therapeutically effective amount of an E-selectin specific monoclonal antibody, or antibody fragment, and a pharmaceutically acceptable carrier.

The invention also provides a method for the treatment of a microbial infection, wherein an E-selectin specific monoclonal antibody is conjugated to an anti-microbial agent.

The invention also provides a method for the treatment of post-reperfusion injury by administering to a patient a pharmaceutical composition containing a therapeutically effective amount of an E-selectin specific monoclonal antibody, or antibody fragment thereof, and a pharmaceutically acceptable carrier.

The invention also provides a method for the treatment of post-reperfusion injury, wherein an E-selectin specific monoclonal antibody is conjugated to an anti-thrombotic agent, antioxidant, anti-complement agent, or anti-inflammatory agent.

The invention also provides a method for the treatment of leukemia or lymphoma by administering to a patient a pharmaceutical composition containing a therapeutically effective amount of an E-selectin specific monoclonal antibody, or antibody fragment, and a pharmaceutically acceptable carrier.

The invention also provides a method for inhibiting the metastatic spread of tumor cells by administering to a patient a pharmaceutical composition containing a therapeutically effective amount of an E-selectin specific monoclonal antibody, or antibody fragment, and a pharmaceutically acceptable carrier.

The invention also provides a treatment of a malignant tumor by administering to a patient a pharmaceutical composition containing a therapeutically effective amount of an E-selectin specific monoclonal antibody, or antibody fragment, and a pharmaceutically acceptable carrier.

The invention also provides a method for the treatment of a malignant tumor, wherein an E-selectin specific monoclonal antibody is conjugated to an anti-tumor agent.

The invention also provides a method for the treatment of vasculitis by administering to a patient a pharmaceutical composition containing a therapeutically effective amount of an E-selectin specific monoclonal antibody, or antibody fragment, and a pharmaceutically acceptable carrier.

The invention also provides a method for the treatment of vasculitis, wherein the E-selectin specific monoclonal antibody is conjugated to an anti-inflammatory agent, anti-thrombotic agent, anti-thrombolytic agent, or anti-complement agent.

The invention also provides a method for the treatment of a vascular smooth muscle cell proliferative disorder by administering to a patient a pharmaceutical composition containing a therapeutically effective amount of an E-selectin specific monoclonal antibody, or antibody fragment, conjugated to an anti-smooth muscle cell proliferative agent, and a pharmaceutically acceptable carrier. In preferred embodiments, the anti-smooth muscle cell proliferative agent is an anti-thrombin agent and the E-selectin specific monoclonal antibody is H18/7 or H4/18. In particularly preferred embodiments, the anti-thrombin agent is hirudin and the E-selectin specific monoclonal antibody is H18/7.

The invention also provides a method for the treatment of acute or chronic allograft rejection by administering to a patient a pharmaceutical composition containing a therapeutically effective amount of an E-selectin specific monoclonal antibody, or antibody fragment, and a pharmaceutically acceptable carrier.

The invention also provides a method for the treatment of acute or chronic allograft rejection, wherein the E-selectin specific monoclonal antibody is conjugated to an anti-inflammatory agent, anti-thrombotic agent, anti-complement agent, or immunosuppressive agent. In particularly preferred embodiments, the E-selectin specific monoclonal antibody is H18/7.

DESCRIPTION OF THE PREFERRED EMBODIMENTS

Figure 1:
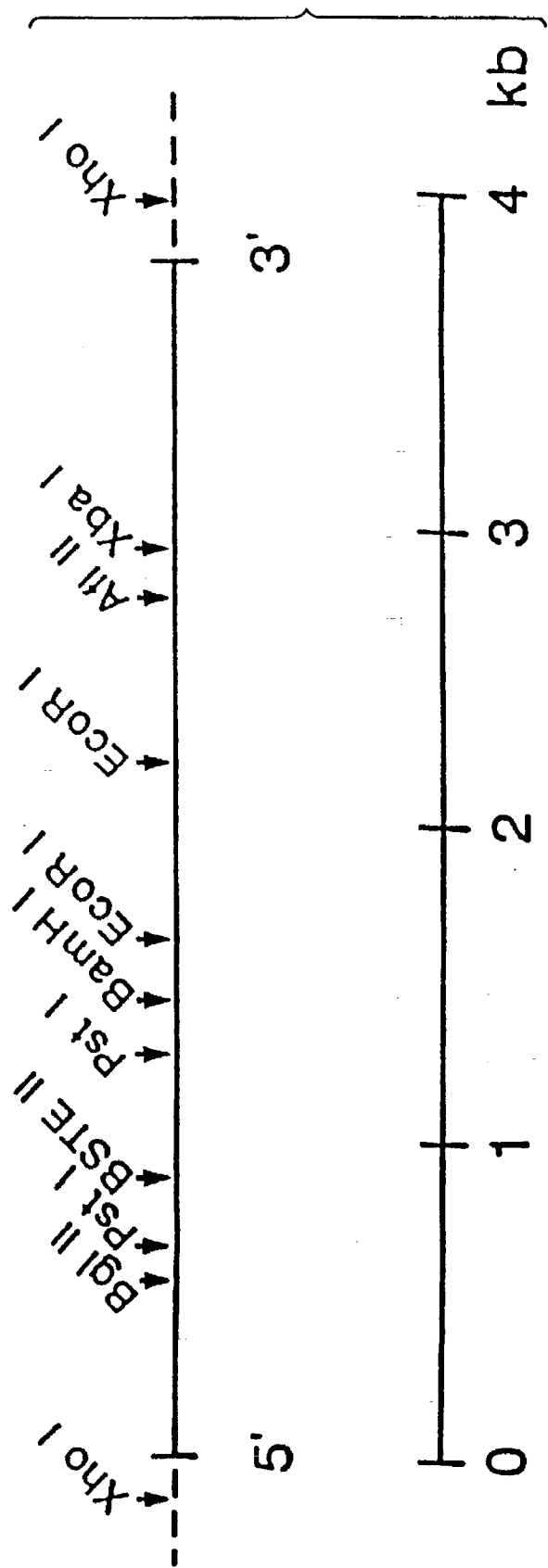
FIG. 1 is an enzyme restriction map of E-selectin cDNA.

The present invention relates to cloned E-selectin genes. cDNA encoding E-selectin may be obtained by the stimulation of cultured human endothelium cells (HEC), isolation of the mRNA, followed by preparation of cDNA by, for example, use of reverse transcriptase according to methods known in the art. Alternatively, episomal DNA may be recovered. The cDNA or episomal DNA is then shotgun cloned, and the resulting clones screened with an antibody that recognizes E-selectin. Alternatively, the clones can be screened with a complementary labeled probe.

The present invention also relates to antibodies that recognize E-selectin. These antibodies can be prepared by immunizing mice with cultured human endothelial cells, which have been activated by, for example, the monokine interleukin 1 (IL 1). Fusion of the splenocytes with myeloma cells and subsequent screening of the hybridomas with IL 1-treated and control HEC allows selection of monoclonal antibodies specific for E-selectin. See Bevilacqua et al., *4th Int'l Symp. Biol. Vasc. Endothelial Cell:*13 (Abstr) (1986); Pober et al., *J. Immunol.* 136:1680–1687 (1986); Bevilacqua et al., in *Leukocyte Immigration and Its Sequelae, Satellite Symp.,* Henry Z. Movat, ed., S. Karger, Basil, Switzerland (1987), pp. 79–93. Bevilacqua et al., *Proc. Natl. Acad. Sci. (USA)* 84:9238–9242 (1987).

Particularly useful monoclonal antibodies for this purpose include H4/18 and H18/7. The hybridoma producing monoclonal antibody H18/7 has been deposited with the American Type Culture Collection (12301 Parklawn Drive, Rockville, Md. 20852) on Jul. 12, 1994 under ATCC Deposit No. HB11684. Other anti-human monoclonal antibodies specific for E-selectin can be used in the methods and immunoconjugates of the invention. These include CL2 (Gundel et al., *J. Clin. Invest.* 88: 1407–1411 (1991); Kishimoto et al., *Blood* 78:805–811 (1991)); CL3 (Mulligan et al., *J. Clin. Invest.* 88: 1396–1406 (1991); Picker et al., *Nature* 349:796–799 (1991)); BB11 (Benjamin et al., *Biochem. and Biophysical Res. Comm.* 171: 348–53 (1990)); and the following monoclonal antibodies disclosed in U.S. Pat. No. 5,011,778 to Newman and Wilson, issued Apr. 30, 1991: 7A9 (ATCC Deposit No. HB 10135), IE7 (ATCC Deposit No. HB 10136), 2G7 (ATCC Deposit No. HB 10137), and 3A2 (ATCC Deposit No. HB 10138).

Antibodies to E-selectin may also be prepared by immunizing mice with recombinant E-selectin, or E-selectin fragments. By "E-selectin fragment" is meant any polypeptide subset of the molecule. Particularly preferred E-selectin fragments include leukocyte-binding fragments and complement-binding fragments. The leukocyte-binding or complement-binding fragments can be obtained by cutting the E-selectin gene with various restriction enzymes or exonucleases, cloning the resulting fragments, and screening for leukocyte or complement binding activity according to methods known in the art. Alternatively, it is possible to analyze the E-selectin structure by a suitable computer program, identify the antigenic regions, and prepare E-selectin fragments by methods of protein synthesis known to those of ordinary skill in the art. Therefore, the invention also relates to antibodies having defined specificity obtained by immunization of an animal with an E-selectin fragment.

The joining of various DNA fragments is performed in accordance with conventional techniques, employing blunt-ended or staggered-ended termini for ligation, restriction enzyme digestion to provide appropriate termini, filling in of cohesive ends as appropriate, alkali and phosphatase treatment to avoid undesirable joining, and ligation with appropriate ligases. The genetic construct may optionally encode a leader sequence to allow efficient expression of the recombinant protein.

To express the recombinant E-selectin, transcriptional and translational signals recognized by an appropriate host element are necessary. Mammalian cells provide post translational modification to recombinant protein molecules that provide for correct folding and glycosylation of appropriate sites. Mammalian cells that may be used in the practice of the invention include COS cells, Chinese hamster ovary (CHO) cells, leukocytes, myeloma cells or other transformed or oncogenic lymphocytes, e.g., EBV-transformed cells, cells of fibroblast origin, such as VERO, or cells of lymphoid origin, such as the hybridoma SP2/0-AG14 or the myeloma P3x63Sgh, and their derivatives. Other hosts include BHK cells and hepatoma cells.

In general, vectors containing replicon and control sequences, which are derived from species compatible with a host cell, are used in connection with the host. The vector ordinarily carries a replicon site, as well as specific genes that are capable of providing phenotypic selection in transformed cells. The expression of the gene-encoding E-selectin can also be placed under control with other regulatory sequences which may be homologous to the cell line in its untransformed state. For example, lactose-dependent E. coli chromosomal DNA comprises a lactose or lac operon which mediates lactose utilization by elaborating the enzyme beta-galactosidase. The lac control elements can be obtained from bacterial phage lambda plac5, which is infective for E. coli. The lac promoter-operator system can be induced by IPTG.

Other promoter/operator systems or portions thereof can be employed as well. For example, colicin E1, galactose, alkaline phosphatase, tryptophan, xylose, and the like can be used.

For mammalian hosts, several possible vector systems are available for expression. One class of vectors utilizes DNA elements that are derived from animal viruses, such as bovine papilloma virus, polyoma virus, adenovirus, vaccinia virus, baculovirus, retroviruses (RSV, MMTV or MOMLV), or SV40 virus. Cells that have stably integrated the DNA into their chromosomes can be selected by introducing one or more markers that allow selection of transfected host cells. The marker may provide for prototropy to an auxotrophic host, biocide resistance, e.g., antibiotics, or heavy metals, such as, copper or the like. The selectable marker gene can be either directly linked to the DNA sequences to be expressed, or introduced into the same cell by cotransformation. Additional elements may also be needed for optimal synthesis of mRNA. These elements include splice signals, as well as transcriptional promoters, enhancers, and termination signals. The cDNA expression vectors incorporating such elements include those described by Okayama, H., Mol. Cel. Biol., 3:280 (1983) and others.

Once the vector or DNA sequence containing the constructs has been prepared for expression, the DNA constructs can be introduced to an appropriate host. Various techniques can be employed, such as protoplast fusion, calcium phosphate precipitation, electroporation or other conventional techniques. After transfection, the cells are grown in media and screened for the appropriate activity using, for example, the above-described antibodies. Expression of the gene(s) results in production of the E-selectin.

The transformed cells can be grown in appropriate nutrient media in culture flasks or injected into a synergistic host, e.g., mouse or a rat, or immunodeficient host or host site, e.g., nude mouse or hamster pouch. In particular, the cells can be introduced into the abdominal cavity of an animal to allow production of ascites fluid that contains E-selectin, or fragment thereof. Alternatively, the cells can be injected subcutaneously, and the E-selectin harvested from the blood of the host. The cells can be used in the same manner as hybridoma cells.

The expressed E-selectin, or fragment thereof, can be isolated from fermentation media or cell culture and purified in accordance with conventional conditions, such as extraction, precipitation, chromatography, affinity chromatography, electrophoresis or the like.

For example, E-selectin can be purified by passing a solution containing the surface protein through a column containing an immobilized antibody that is specific for E-selectin, for example, the above-described antibodies H18/7 and H4/18. The desired protein can then be eluted by raising the pH of the eluant.

E-selectin, or a structurally homologous molecule, may be involved in mediating cell-cell interactions in embryogenesis/organ development; in neoplasia (with possible expression by tumor cells); in wound/tissue regeneration; and in related processes involving activated endothelium. Therefore, administration of E-selectin, or fragments thereof, is useful as a therapeutic intervention and/or a diagnostic tool for investigation of these processes.

The present invention also relates to a method of selectively targeting a therapeutic agent to a site of activated endothelium, comprising administering to a patient a pharmaceutical composition comprising a therapeutically effective amount of an E-selectin specific monoclonal antibody, or antibody fragment, conjugated to a therapeutic agent, and a pharmaceutically acceptable carrier. As used herein, the term "activated endothelium" refers to vascular endothelial cells that have been induced by cytokines such as IL-1 and TNF as well as bacterial endotoxin LPS, to express E-selectin.

"Therapeutic agent" as used herein includes anti-thrombotic agents, thrombolytic agents, anti-inflammatory agents, antioxidants, anti-tumor agents, anti-smooth muscle cell proliferative agents, anti-complement agents, immunosuppressive agents, or anti-microbial agents.

"Anti-thrombotic agent" as used herein includes any agent that inhibits the formation of a thrombus. The term "anti-thrombotic agent" encompasses both direct thrombin inhibitors and indirect thrombin inhibitors (See Table I, Lefkovits and Topol, Circulation 90:1522 (1994)), as well as other agents that act independently of thrombin inhibition.

Examples of indirect thrombin inhibitors include heparin, low molecular weight heparins, heparinoids, and ATIII. Direct thrombin inhibitors, which can also be called anti-thrombin agents, include any agent that directly antagonizes and inhibits the biochemical and/or cellular actions of thrombin. Representative examples of these "antithrombin agents" include hirudin (and recombinant variants), hirulog, hirugen, argatroban, and PPACK. Anti-thrombotic agents that act independently of thrombin inhibition include platelet inhibitors, such as aspirin.

"Thrombolytic agent" as used herein includes any agent that is utilized for inducing or initiating the lysis of a thrombus. Representative examples include tissue plasminogen activator (tPA), streptokinase, urokinase, or eminase.

"Anti-inflammatory agent" as used herein includes any agent that reduces inflammation of an affected blood vessel and/or adjacent tissue, which has developed in response to injury or abnormal stimulation. Representative examples include aspirin, acetaminophen, nonsteroidal anti-inflammatory drugs (NSAIDs), glucocorticoids, and antihistamines.

"Antioxidant" as used herein includes any agent capable of inhibiting oxidation. Representative examples include alpha-tocopherol (Vitamin E), ascorbic acid (Vitamin C), Vitamin A (usually in the form of beta-carotene) and probucol.

"Anti-smooth muscle cell proliferative agent" as used herein includes any agent that inhibits the proliferation and/or migration of smooth muscle cells, as would be seen in vascular smooth muscle cell proliferative disorders, such as, atherosclerosis or post-angioplasty restenosis. These agents include anti-thrombin agents, as defined above, as well as agents that would inhibit endothelial derived smooth muscle cell directed growth factors, such as anti-platelet derived growth factor (PDGF).

"Anti-complement agent" as used herein includes any agent that interferes with, inhibits, or prevents the activation of at least one type of complement protein. Representative agents include complement receptor 1 (CR1), soluble CR1 (sCR1), decay-accelerating factor (DAF), membrane cofactor protein (MCP), factor H, and C4-binding protein (C4-bp). See Weisman et al., Science 249:146–151 (1990), and the references cited therein, for a general discussion of these agents.

"Immunosuppressive agent" as used herein includes any agent that suppresses the development of at least one type of immune response. Representative agents include cyclosporin A, azathioprine, and methotrexate.

Monoclonal antibodies directed to E-selectin are used in the method of the invention. Preferably, H18/7 or H4/18 is used, although other anti-human monoclonal antibodies to E-selectin can be utilized, as was discussed supra.

The term "conjugated to a therapeutic agent" as used herein refers to the firm attachment of the therapeutic agent to the E-selectin monoclonal antibody. Such attachment may be covalent or noncovalent, although it is preferably covalent. The conjugation of the monoclonal antibody to the therapeutic agent may be direct or, most commonly, by means of a coupling or conjugating agent. There are several intermolecular cross-linking reagents that can be utilized (See, e.g., Means and Feeney, *Chemical Modification of Proteins*, Holden-Day, (1974), pp. 39–43). Among these reagents are, for example, N-succinimidyl 3-(2-pyridyldithio) propionate (SPDP) or N-N'-(1,3-phenylene) bismaleimide (both are highly specific for sulfhydryls, and form irreversible linkages); N-N'-ethylene-bis-(iodoacetamide) or other such reagent having 6 and 11 carbon methylene bridges (relatively specific for sulfhydryl groups); 1,5-di-fluoro-2,4-dinitrobenzene (forms irreversible linkages with amino and tyrosine groups); p,p'-difluoro-m-m'-dinitrodiphenylsulfone (forms irreversible cross-linkages with amino and phenolic groups); dimethyl adipimidate (specific for amino groups); phenyl-2-4-disulfonylchloride (reacts principally with amino groups); hexamethylenediisocyanate or diisothiocyanate, or azophenyl-p-diisocyanate (reacting principally with amino groups); glutaraldehyde (reacting with several different side chains) and bis-diazobenzidine (reacting primarily with tyrosine and histidine). These are only a few of several cross-linking agents that be utilized. The conditions and concentrations useful for obtaining the monoclonal antibody/therapeutic agent conjugate of the invention can be readily adjusted by those of skill in the art by reference to known literature or by no more than routine experimentation.

The invention also relates to an immunoconjugate for selectively targeting a therapeutic agent to a site of activated endothelium in a patient, comprising a monoclonal E-selectin specific antibody, or fragment thereof, and a therapeutic agent that is an anti-thrombotic agent, thrombolytic agent, anti-inflammatory agent, antioxidant, antitumor agent, anti-smooth muscle cell proliferative agent, anti-complement agent, immunosuppressive agent, or antimicrobial agent.

E-selectin, or fragments thereof, can be administered to a patient to treat intimation. A soluble form of E-selectin can block leukocyte adhesion to endothelium at sites of inflammation. In addition, the primary structure of E-selectin derived from amino acid sequence analysis suggests that E-selectin binds proteins of the complement system. Therefore, administration of E-selectin, or the complement or leukocyte-binding fragment thereof, would regulate complement activation and inhibit its pathophysiological consequences.

It is also possible to block inflammation by administering to a patient a monoclonal antibody directed toward E-selectin. Such monoclonal antibodies include the above-described monoclonal antibodies H18/7 and H4/18. Other anti-human monoclonal antibodies that are specific for E-selectin can also be utilized, as discussed previously. The monoclonal antibodies can also comprise antibody fragments, for example, F(ab')2 fragments, which minimize immunological reaction due to the Fc portion of the immunoglobulin.

In a preferred embodiment, an E-selectin specific monoclonal antibody is conjugated to an anti-inflammatory agent, such as aspirin, acetaminophen, nonsteroidal anti-inflammatory (NSAIDS) drugs, glucocorticoids or antihistamines, in order to treat inflammation.

E-selectin is also useful for the treatment of microbial infections. A variety of microbes (bacteria, rickettsia, borrelia, various parasites, and viruses) bind to vascular endothelium in some cases, possibly, by an E-selectin dependent mechanism. Thus, E-selectin, or a leukocyte-binding fragment thereof, can be administered to a patient to prevent the binding of microbes that recognize E-selectin as a binding target molecule and thereby, treat microbial infections.

The invention also relates to a treatment for microbial infections comprising administering a pharmaceutical composition comprising E-selectin, or a fragment thereof, that is coupled to an antimicrobial agent. Such a conjugate specifically delivers and localizes the anti-microbial agent to the site of vascular infection.

Moreover, it is also possible to administer an antibody or antibody fragment directed to E-selectin to block the microbe receptor on endothelial tissue. Thus, the invention also relates to the treatment of microbial infections comprising administering a monoclonal antibody, or antibody fragment, directed to E-selectin to a patient.

In another embodiment, the invention also relates to a method of treating microbial infection by administering a pharmaceutical composition comprising an antibody to E-selectin conjugated to an anti-microbial agent. Such a conjugate specifically targets the activated endothelium caused by microbial infection and specifically delivers an anti-microbial agent to the site of vascular infection.

Such antimicrobial agents include ricin or diphtheria toxin, as described above, or can comprise halogenated amino acids that act as suicide enzyme inhibitors. See Soper et al., *J. Biol. Chem.* 252:3170–3175 (1977) (β-chloroalanine); Kollonitsch. et al., *J. Amer. Chem. Soc.* 98:5591–5593 (1976) (3-fluoroalanine); Wang et al., *Biochemistry* 17:1313–1321 (1978) (β,β-difluoroalanine and β,β,β-trifluoroalanine).

Administration of E-selectin, or fragment thereof, may also be used for the prevention of post-reperfusion injury. When treating arterial thrombosis, induction of reperfusion by clot lysing agents such as tissue plasminogen activator (t-PA), is often associated with tissue damage. Such tissue damage is thought to be mediated, at least in part, by polymorphonuclear leukocytes (PMN). Therefore, administration of E-selectin, or a fragment thereof, preferably, a leukocyte-binding fragment, would block PMN-endothelial interactions, and thereby diminish or prevent post-reperfusion injury.

Alternatively, it is also possible to administer an antibody directed toward E-selectin to a patient to block PMN-endothelial interactions, and thereby prevent or treat inflammation. Suitable antibodies for this purpose include H18/7 and H4/18, or an antibody fragment thereof. Again, other anti-human monoclonal antibodies that are specific for E-selectin can also be utilized, as was discussed supra.

In another embodiment for treating post-reperfusion injury, an E-selectin specific monoclonal antibody is conjugated to an anti-thrombotic agent, antioxidant, anti-complement agent, or anti-inflammatory agent. In this way, the chosen therapeutic agent is specifically targeted to the site of activated vascular endothelium, which is a consequence of post-reperfusion injury.

E-selectin, or leukocyte-binding fraction thereof, can also be administered to a patient to prevent adhesion of leukocyte tumor cells or non-leukocyte tumor cells to endothelial tissue. Thus, administration of E-selectin, or leukocyte-binding fragment thereof could prevent metastatic spread of tumor cells. Alternatively, antibodies directed to E-selectin, or antibody fragments, can be administered to block the adhesion of tumor cells to endothelial tissue, thereby inhibiting metastatic spread.

In addition, E-selectin, or a leukocyte-binding fragment thereof, can be coupled to a chemotherapeutic drug that could bind to tumor cells expressing receptors for E-selectin, to kill the tumor cell. Thus, the invention also relates to a method for treating, for example, leukemia or lymphoma comprising administering to a patient E-selectin, or a leukocyte-binding fragment thereof, that is coupled to an anti-tumor agent. Such antitumor agents include, for example, bacterial toxins, such as, diphtheria toxin or ricin, a toxic lectin.

Thus, the invention also relates to fusion proteins comprising E-selectin, or leukocyte-binding fragment thereof, coupled to a second protein comprising diphtheria toxin or ricin. Methods for producing fusion proteins comprising fragment A of diphtheria toxin by recombinant means are taught in U.S. Pat. No. 4,675,382 (1987). Diphtheria toxin contains two polypeptide chains. The B chain binds the toxin to a receptor on a cell surface. The A chain actually enters the cytoplasm and inhibits protein synthesis by inactivating elongation factor 2, the factor that translocates ribosomes along mRNA concomitant with hydrolysis of ATP. See Darnell, J. et al., in *Molecular Cell Biology*, Scientific American Books, Inc. (1986), p. 662. In a preferred embodiment, the fusion protein of the invention comprises E-selectin, or a leukocyte-binding fragment thereof, and the A chain of diphtheria toxin.

The invention also relates to the treatment of a malignant tumor by administering to a patient a pharmaceutical composition comprising a therapeutically effective amount of an E-selectin-specific monoclonal antibody, or antibody fragment, either alone or conjugated to an anti-tumor agent, as discussed previously. In this case, the monoclonal antibody to E-selectin would specifically bind to the E-selectin that is expressed by the activated endothelium resulting from the neoplastic condition. Thus, an anti-tumor agent, conjugated to an E-selectin monoclonal antibody, would specifically and selectively deliver the anti-tumor agent to the site of the malignant tumor.

The invention also relates to a method of treating vasculitis by administering E-selectin, or a fragment thereof, to a patient. Recent evidence suggests that tissue damage in certain forms of vasculitis involves induced endothelial surface proteins. Thus, E-selectin may be a target for antibody-mediated or cell-mediated damage of the vessel wall.

The invention also relates to a method of treating vasculitis by administering to a patient an antibody to E-selectin, or antibody fragment. In a preferred embodiment, an E-selectin monoclonal antibody is conjugated to an anti-inflammatory agent, anti-thrombotic agent, anti-thrombolytic agent, or anti-complement agent, in order to specifically deliver the therapeutic agent to the site of activated endothelium caused by the vasculitis.

The invention also relates to a method for the treatment of a vascular smooth muscle cell proliferative disorder by administering to a patient a pharmaceutical composition comprising a therapeutically effective amount of an E-selectin specific monoclonal antibody, or antibody fragment, conjugated to an anti-smooth muscle cell proliferative agent.

By "smooth muscle cell proliferative disorder" is meant a disorder, such as atherosclerosis or post-angioplasty restenosis, that is characterized by the proliferation of smooth muscle cells. Both atherosclerosis and post-angioplasty restenosis are characterized by cytokine-activated vascular endothelial cells that express E-selectin on the cell surface. When vascular endothelium is damaged, as in these states, thrombin occupies receptors on the endothelium and smooth muscle cells to activate cellular proliferation (Graham and Alexander, *J. Vasc. Surg.* 11:307–313 (1990), as well as stimulate the release of platelet-derived growth factor (PDGF) (Harlan et al., *J. Cell. Biol.* 103:1129–1133 (1986)). Thrombin generation is predicted to be an important component of vascular "response to injury" processes such as atherosclerosis and post-angioplasty restenosis. Thus, the invention relates to the specific targeting of an anti-smooth cell proliferative agent, such as an anti-thrombin agent or an anti-platelet derived growth factor, to the site of proliferation or migration of smooth muscle cells (i.e., in atherosclerosis or post-angioplasty restenosis) by conjugating the agent to an E-selectin specific monoclonal antibody.

In a preferred embodiment, the anti-smooth muscle cell proliferative agent is an anti-thrombin agent. A particularly preferred anti-thrombin agent is hirudin. The E-selectin specific monoclonal antibody is preferably H18/7 or H4/18, but other anti-human monoclonal antibodies against E-selectin can be used, as described supra.

Finally, the invention also relates to a method for the treatment of acute or chronic allograft rejection by administering to a patient a pharmaceutical composition comprising a therapeutically effective amount of an E-selectin specific monoclonal antibody, or antibody fragment.

By "allograft" is meant a transplanted tissue or organ, wherein the donor and recipient are genetically different.

By "allograft rejection" is meant a condition whereby a transplant recipient mounts a cellular and/or humoral immune response against the allograft, sometimes threatening the survival of the graft and possibly the graft recipient. The numerous mechanisms associated with allograft rejection, such as the production of immune complexes and the activation of complement, can induce endothelial damage. Platelet aggregation and thrombosis can occur following such endothelial damage.

Activation of the immune response, as occurs during the process of allograft rejection, involves the synthesis and release of a variety of cytokines leading to endothelial activation, and consequently the expression of adhesion molecules by endothelial cells. See, e.g., Briscoe et al., "Predictive Value of Inducible Endothelial Cell Adhesion Molecule Expression for Acute Rejection of Human Cardiac Allografts," *Transplantation* (1995) (in press). Induction of the expression of E-selectin has been reported to occur during the course of renal and cardiac allograft rejection (Taylor et al., *Transplantation* 54:451 (1992); Brockmeyer et al., *Transplantation* 55:610 (1993); Fuggle et al., *Transplantation* 55:117 (1993)).

Thus, the administration of an E-selectin specific monoclonal antibody, or antibody fragment, can block leukocyte adhesion that occurs during acute or chronic allograft rejection, and can therefore be used to treat, or even prevent, such a condition.

In a preferred embodiment for treating acute or chronic allograft rejection, an E-selectin specific monoclonal antibody is conjugated to an anti-inflammatory agent, anti-thrombotic agent, anti-complement agent, or immunosuppressive agent. In this way, the conjugate would specifically deliver the therapeutic agent to the site of activated vascular endothelium, which is a consequence of acute or chronic allograft rejection.

The E-selectin molecule, or fragment thereof, antibodies and antibody fragments directed to E-selectin, or antibodies conjugated to a therapeutic agent, can be formulated into pharmaceutically useful compositions according to known methods, such as by admixture with a pharmaceutically acceptable carrier vehicle. Suitable vehicles and their formulation are described, for example, in *Remington's Pharmaceutical Sciences* (16th ed.), Osol, A., ed., Mack Publishing Company, Easton, Pa. (1980). In order to form a pharmaceutically acceptable composition suitable for effective administration, such compositions will contain a therapeutically effective amount of the E-selectin, fragment of E-selectin, antibody or antibody fragment directed to E-selectin, or antibody directed to E-selectin that is conjugated to a therapeutic agent, either alone or with a suitable amount of carrier vehicle.

When used for the treatment of inflammation, post-reperfusion injury, leukemia, lymphoma, microbial/parasitic infection, vascular smooth muscle cell proliferative disorders, vasculitis, acute or chronic allograft rejection, or inhibition of the metastatic spread of tumor cells, the pharmaceutical composition can comprise from 1 pg/kg to 10 mg/kg patient of E-selectin, fragment of E-selectin, or fusion protein of the invention, although higher or lower doses are possible. When used for the purpose of treating inflammation, microbial/parasitic infection, post-reperfusion injury, leukemia, lymphoma, vascular smooth muscle cell proliferative disorders, vasculitis or inhibition of the metastatic spread of tumor cells, the pharmaceutical composition can comprise from 1 pg/kg to 10 mg/kg patient of E-selectin-specific antibody or antibody fragment thereof, although higher or lower doses are possible.

Additional pharmaceutical methods can be employed to control the duration of action. Controlled release preparations can be achieved by the use of polymers to complex or absorb the E-selectin, E-selectin fragment, E-selectin-specific antibody, or antibody fragment, of the invention. Controlled delivery may be achieved by selecting appropriate macromolecules (for example, polyesters, polyamino acids, polyvinyl pyrrolidone, ethylenevinylacetate, methylcellulose, carboxymethylcellulose, protamine sulfate, or lactide/glycolide copolymers). The rate of drug release can also be controlled by altering the concentration of such macromolecules. Another possible method for controlling the duration of action comprises incorporating the therapeutic agents into particles of a polymeric substance, such as, polyesters, polyamino acids, hydrogels, polylactide/glycolide copolymers, or ethylenevinylacetate copolymers. Alternatively, it is possible to entrap the therapeutic agents in microcapsules prepared, for example, by coacervation techniques or by interfacial polymerization, for example, by the use of hydroxymethylcellulose or gelatin-microcapsules or poly(methylmethacrylate) microcapsules, respectively, or in a colloid drug delivery system, for example, liposomes, albumin microspheres, microemulsions, nanoparticles, nanocapsules, or in macroemulsions. Such teachings are disclosed in *Remington's Pharmaceutical Sciences* (1980).

E-selectin, a fragment of E-selectin, antibody or antibody fragments directed to E-selectin, or E-selectin antibody or antibody fragments conjugated to a therapeutic agent, can be administered to a patient by means well known in the art. Such means of introduction include oral means, intranasal means, subcutaneous means, intramuscular means, intravenous means, intra-arterial means, or parenteral means.

The invention also relates to a method of detecting E-selectin expression in a patient, comprising administering to a patient a pharmaceutical composition comprising a detectable amount of a labeled E-selectin specific antibody, or antibody fragment, and a pharmaceutically acceptable carrier; and detecting the label.

Preferably, the labels that can be detected within the body of a patient include, but are not limited to, radiopaque labels, radiolabels or paramagnetic isotopes. This method allows the detection and localization of E-selectin expression in a patient, which is associated with various disease states.

After the E-selectin specific antibody, or antibody fragment, has been administered and sufficient time has passed for the antibody to localize at the site of E-selectin expression and unbound antibody has been permitted to clear from healthy tissue in the patient, the label can be detected. Where the label is a radionuclide, it must be of the type of decay that is detectable for a given type of instrument. Further, the radionuclide for in vivo diagnosis should have a half-life long enough to be still detectable at the time of maximum uptake, but short enough that after diagnosis unwanted radiation does not remain in the patient. Coupling of the radionuclides to the antibody or antibody fragment is known in the art and is often accomplished either directly or indirectly using an intermediary functional group. Examples of radioisotopes that can be used for in vivo diagnosis are $^{99m}$Tc, $^{123}$I, $^{131}$I, $^{111}$In, $^{97}$Ru, $^{67}$Cu, $^{67}$Ca, $^{68}$Ga, $^{72}$As, $^{89}$Zr, and $^{201}$Tl.

Paramagnetic isotopes for purposes of in vivo diagnosis can also be used according to the methods of this invention. Examples of elements that are particularly useful for use in Magnetic Resonance Energy techniques include $^{157}$Gd, $^{55}$Mn, $^{162}$Dy, $^{52}$Cr, and $^{56}$Fe.

A method for detecting E-selectin expression in a patient, comprising administering a pharmaceutical composition comprising a detectable amount of a labelled anti-E-selectin H18/7 monoclonal antibody, or labelled antibody fragment comprising a Fab domain, is the claimed subject matter of the parent application Ser. No. 08/102,510 now U.S. Pat. No. 5,403,713.

It is also possible to use antibodies directed to E-selectin to detect the presence of E-selectin in biological samples, such as blood, serum, cerebrospinal fluid, etc., as an indication of expression of E-selectin in association with various disease processes.

The detection and quantitation of antigenic substances and biological samples frequently utilize immunoassay techniques. These techniques are based upon the formation of a detectable complex between the antigenic substance being assayed, e.g., E-selectin, and an antibody or antibodies in which one or the other member of the complex may be delectably labeled. In the present invention, the E-selectin specific antibody can be labeled with any conventional label.

Thus, in this aspect of the invention, a biological sample can be treated with nitrocellulose, or other solid support that is capable of immobilizing cells, cell particles, or soluble protein. The support can then be washed with suitable buffers followed by treatment with the delectably labeled E-selectin specific antibody. The solid phase support can then be washed with the buffer a second time to remove unbound antibody. The amount of bound label on the antibody can then be detected by conventional means.

In carrying out the assay of the present invention on a sample containing E-selectin or cells expressing E-selectin on their surface, the process comprises:

(a) contacting a sample suspected of containing E-selectin or cells expressing E-selectin on its surface with a solid support to effect immobilization of E-selectin or cells expressing E-selectin on its surface;

(b) contacting said solid support with a delectably labeled E-selectin specific antibody;

(c) incubating said detectably labeled E-selectin specific antibody in contact with said support for a time sufficient to allow the E-selectin specific antibody to bind to the immobilized E-selectin or cells expressing E-selectin on its surface;

(d) separating the solid phase support from the incubation mixture obtained in step (c); and (e) detecting the bound label and thereby detecting and quantifying E-selectin or cell expressing E-selectin on its surface.

Alternatively, labeled E-selectin specific antibody/E-selectin complex in a sample can be separated from a reaction mixture by contacting the complex with an immobilized antibody or protein that is specific for an immunoglobulin, e.g., protein A, protein G, anti-IgM or anti-IgG antibodies. Such anti-immunoglobulin antibodies can be monoclonal or polyclonal. The solid support can then be washed with a suitable buffer to give an immobilized E-selectin/labeled E-selectin specific antibody complex. The label on the fusion protein can then be detected to give a measure of endogenous E-selectin and, thereby, the extent of stimulated endothelial cells.

Thus, the invention relates to a method for detecting E-selectin or leukocyte-binding fragment thereof in a sample comprising (a) contacting a sample suspected of containing E-selectin with an E-selectin specific antibody or fragment thereof which binds to E-selectin; and (b) detecting whether a complex is formed.

The invention also relates to a method of detecting E-selectin or leukocyte-binding fragment thereof in a sample, further comprising (c) contacting the mixture obtained in step (a) with an Fc binding molecule, such as an antibody, protein A, or protein G, which is immobilized on a solid phase support and is specific for the E-selectin specific antibody to give a E-selectin/E-selectin specific antibody-immobilized antibody complex;

(d) washing the solid phase support obtained in step (c) to remove unbound E-selectin/E-selectin specific antibody complex; and (e) detecting the label on the E-selectin specific antibody.

Of course, the specific concentrations of detectably labeled antibody and E-selectin, the temperature and time of incubation, as well as other assay conditions can be varied, depending on various factors including the concentration of E-selectin in the sample, the nature of the sample, and the like. Those skilled in the art will be able to determine operative and optimal assay conditions for each determination by employing routine experimentation.

Other such steps as washing, stirring, shaking, filtering, and the like may be added to the assays as is customary or necessary for the particular situation.

One of the ways in which the E-selectin specific antibody can be detectably labeled is by linking the same to an enzyme. This enzyme, in turn, when later exposed to its substrate, will react with the substrate in such a manner as to produce a chemical moiety that can be detected, for example, by spectrophotometric, fluorometric, or visual means. Enzymes that can be used to detectably label the E-selectin specific antibody include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase, and acetylcholine esterase.

The E-selectin specific antibody can also be labeled with a radioactive isotope that can be determined by such means as the use of a gamma counter or a scintillation counter or by autoradiography. Isotopes that are particularly useful for the purpose of the present invention are: $^{3}$H, $^{125}$I, $^{131}$I, $^{32}$P, $^{35}$S, $^{14}$C, $^{51}$Cr, $^{36}$Cl, $^{57}$Co, $^{58}$Co, $^{59}$Fe and $^{75}$Se.

It is also possible to label the E-selectin specific antibody with a fluorescent compound. When the fluorescently labeled antibody is exposed to light of the proper wave length, its presence can then be detected, owing to the fluorescence of the dye. Among the most commonly used fluorescent labelling compounds are fluorescein isothiocyanate, rhodamine, phycoerytherin, phycocyanin, allophycocyanin, o-phthaldehyde, and fluorescamine.

The E-selectin specific antibody can also be detectably labeled using fluorescence emitting metals such as $^{152}$Eu, or others of the lanthanide series. These metals can be attached to the E-selectin specific antibody using such metal chelating groups as diethylenetriaminepentaacetic acid (DTPA) or ethylenediaminetetraacetic acid (EDTA).

The E-selectin specific antibody also can be detectably labeled by coupling it to a chemiluminescent compound. The presence of the chemiluminescent-tagged E-selectin specific antibody is then determined by detecting the presence of luminescence that arises during the course of a chemical reaction. Examples of particularly useful chemiluminescent labeling compounds are luminol, isoluminol, theromatic acridinium ester, imidazole, acridinium salt, and oxalate ester.

Likewise, a bioluminescent compound can be used to label the E-selectin specific antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase, and aequorin.

Detection of the E-selectin specific antibody can be accomplished by a scintillation counter, for example, if the detectable label is a radioactive gamma emitter, or by a fluorometer, for example, if the label is a fluorescent material. In the case of an enzyme label, the detection can be accomplished by colorimetric methods that employ a substrate for the enzyme. Detection may also be accomplished by visual comparison of the extent of enzymatic reaction of a substrate in comparison with similarly prepared standards.

Having now generally described this invention, it will be better understood by reference to certain specific examples. These examples are included herein for purposes of illustration only, and are not intended to be limiting of the invention unless otherwise specified.

EXAMPLE 1

Molecular Cloning of E-selectin

A cDNA library was constructed using RNA obtained from cultured HEC that had been treated for 2 hours with rIL-1β (5 U/mL). The library was transfected into COS cells and Mabs H18/7 and H4/18 were used to isolate cells expressing E-selectin epitopes. Episomal DNA was recovered, expanded in bacteria (mc 1061p3), and subjected to two more rounds of expression-panning (Seed et al., *Proc. Natl. Acad. Sci. (USA)* 84:3365–3369 (1987); Aruffo et al., *Proc. Natl. Acad. Sci. (USA)* 84:8573–8577 (1987)) to obtain a cDNA clone designated pE-selectin. COS cells transfected with pE-selectin expresses a molecule(s) reactive with both Mab H18/7 and H4/18, but not with control Mabs, as detected by indirect immunofluorescence and immunoperoxidase.

Mab H18/7 immunoprecipitated two polypeptides of Mr 115,000 and 97,000 from biosynthetically labeled, rIL-1 stimulated HEC but not from control HEC. Two proteins of similar mass (Mr 107,000 and 97,000) were obtained from biosynthetically labeled, pE-selectin transfected COS cells.

The lower molecular mass of the COS cell product is consistent with previous observations (Seed et al., supra; Aruffo et al., supra), and may reflect altered glycosylation. Treatment of both the COS cell and HEC derived immunoprecipitates with N-glycosidase F (N-Glycanase, Genzyme Inc., Boston, Mass.) to remove N-linked carbohydrates, yielded a single band by electrophoresis corresponding to a polypeptide(s) of Mr 77,000. These data suggest that the polypeptide backbone of recombinant, COS cell-derived E-selectin is equivalent to that of natural, endothelial cell-derived E-selectin. In addition, it is consistent with the hypothesis that the two species immunoprecipitated from biosynthetically labeled cells contain the same polypeptide backbone and differ in post-translational modification. This hypothesis is further supported by pulse-chase biosynthetic labeling experiments using rIL-1β stimulated HEC and pE-selectin transfected COS cells. In both cases, label is first seen associated with the lower molecular mass protein (Mr 97,000), followed by an apparent "chasing" of the label into the upper molecular mass form. Taken together, these data strongly suggest that the two species immunoprecipitated with anti-E-selectin Mabs are related as precursor and product.

EXAMPLE 2

Primary Structure and Homologies

As represented in FIG. 1, pE-selectin was found to be 3.85 kb with a short 5' untranslated region, a 1,830 base open reading frame, and a relatively long (1.9 kb) 3' untranslated region. The nucleotide sequence of the cDNA encoding E-selectin and the 3' untranslated region is shown in SEQ ID NO:1, as well as in the parent application, which is now U.S. Pat. No. 5,403,713. The nucleotide sequence of the cDNA encoding E-selectin is shown in SEQ ID NO:2, as well as in the parent application, which is now U.S. Pat. No. 5,403,713.

The translated amino acid sequence of E-selectin is shown in SEQ D NO:3, as well as in the parent application, which is now U.S. Pat. No. 5,403,713.

The translated amino acid sequence of pE-selectin suggests typical features of a transmembrane protein. For example, the extracellular domain contains eleven potential N-linked glycosylation sites.

EXAMPLE 3

Functional Studies

Mab 18/7 inhibits the adhesion of PMN (>50%) and HL-60 cells (>60%) to activated HEC monolayers (Bevilacqua et al., *Proc. Natl. Acad. Sci., USA* 84:9238–9242 (1987)). From these studies, it appeared that E-selectin may promote leukocyte adhesion by acting as a ligand for a leukocyte cell surface receptor. This hypothesis is further supported by the present studies using cloned E-selectin. Transfection of COS cells with pE-selectin promotes the adhesion of HL-60 cells. Immunoperoxidase staining revealed a direct correlation between COS cell expression of E-selectin and HL-60 cell adhesion. Mab H18/7 was found to abate (100±3% inhibition, mean ±SEM, 3 exp.), the augmented adhesion to pELAM transfected COS cells.

EXAMPLE 4

Expression of Natural E-selectin

Figure 2:
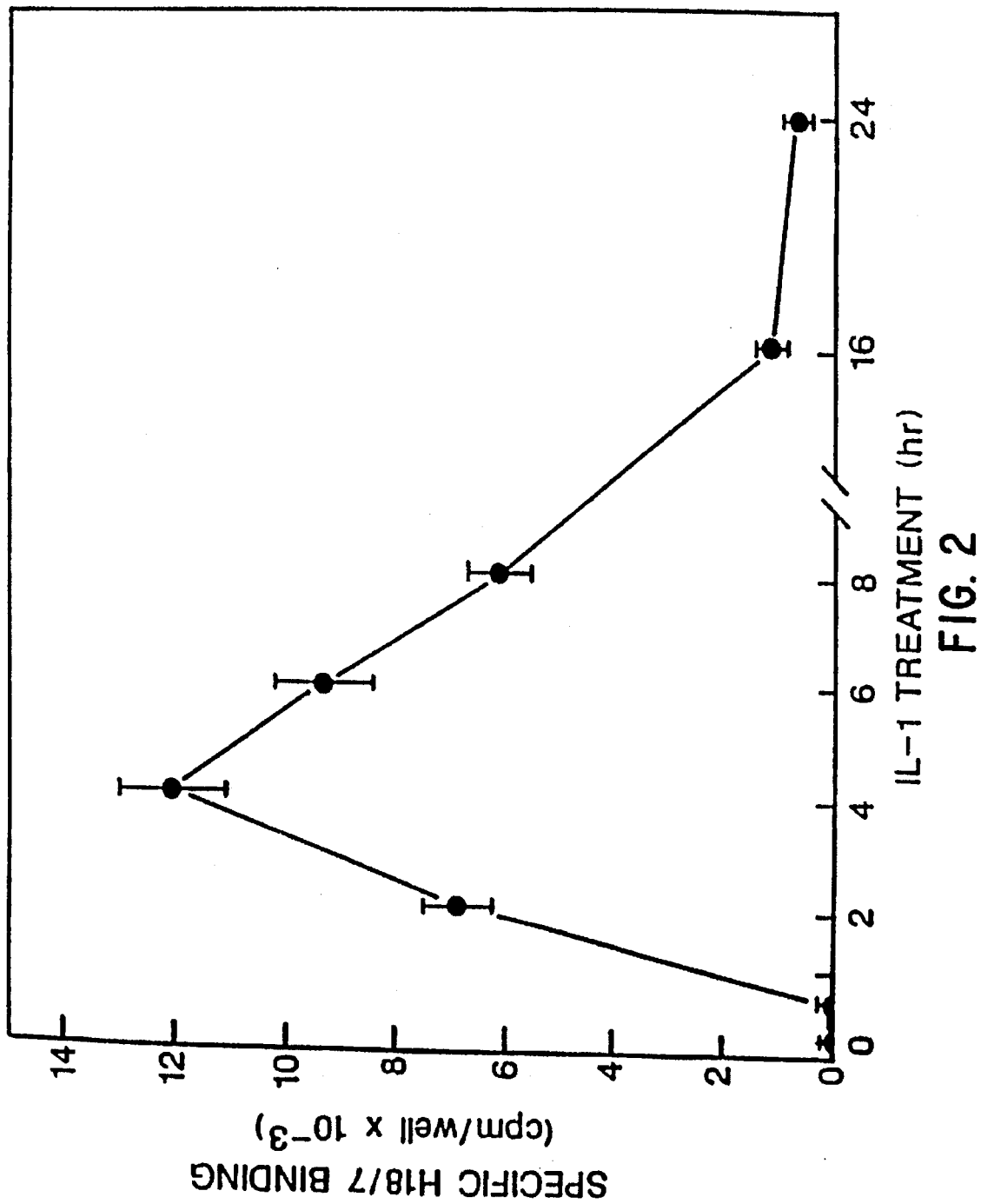
FIG. 2 is a graph showing the specific binding of H18/7 to HEC monolayers for various times after treatment with IL-1.

Previous studies have demonstrated that unstimulated HEC express little or no E-selectin. Id. Treatment of HEC monolayers for 4 hours with rIL-1 (5 U/mL) or rTNF (200 U/mL) resulted in the production of anti-E-selectin precipitable species. Similar results were obtained with lymphotoxin (200 U/mL) and bacterial endotoxin (10 µg/mL). No induction of E-selectin was observed after treatment of the HEC with IFN (200 U/mL). RNA blot analysis showed a primary species of 3.9 kb in HEC treated for 2 hr with rIL-1 or rTNF, that was absent in unstimulated and IFN-stimulated HEC. Continuous exposure of HEC monolayers to rIL-1 results in a rapid increase in the expression of E-selectin with onset at 1–2 hr, and peak at 4–6 hr, followed by a decline toward basal levels by 24 hrs. As shown in FIG. 2, endothelial cell surface expression of E-selectin, as detected in an immunobinding assay, correlates temporally with the expression of E-selectin mRNA. Thus, endothelial cell expression of E-selectin can be induced by several mediators including rIL-1 and rTNF. These effects are time-dependent and appear to occur, at least in part, at a transcriptional level. Blot hybridization of genomic DNA from placenta revealed a pattern consistent with a single-copy gene.

Conclusions

E-selectin is a novel cell surface glycoprotein with sequence homologies to a variety of complement binding proteins including complement receptor 1 (CR1), complement receptor 2 (CR2), complement Factor H and C4 binding protein as well as some complement-binding proteins such as $\beta_2$-glycoprotein I. These homologies suggest the existence of a family of related proteins. The translated amino acid sequences of E-selectin reveal typical features of a transmembrane protein including a leader sequence. The extracellular domain contains eleven potential N-linked glycosylation sites and studies with endoglycosidase H suggest that N-linked carbohydrates account for about 40% of the total molecular mass (Mr 115,000) of mature endothelial E-selectin. In addition, these studies, in conjunction with pulse-chase labeling procedures, provide strong evidence that the two polypeptides immunoprecipitated from activated HEC by anti-E-selectin Mabs are composed of the same polypeptide backbone; the difference in molecular mass between the two species appears to involve post-translational modification, probably at the level of carbohydrate processing.

The inducible expression of E-selectin may be of central importance in its role in leukocyte-vessel wall interactions. The data indicate that certain inflammatory/immune cytokines including IL-1 and TNF, but not IFN-, act on endothelial cells to induce the biosynthesis and expression of E-selectin. RNA blot analysis suggests that the induction of E-selectin occurs, in large part, at the transcriptional level. Previous studies with Mab H4/18 have demonstrated focal endothelial expression of E-selectin in a variety of pathophysiological settings.

EXAMPLE 5

Immunotargeting of an Anti-Thrombin Agent to Activated Endothelial Cells Using the Monoclonal Antibody H18/7

In this example, an immunoconjugate was designed to target the thrombin inhibitor, hirudin, to the surface of activated endothelial cells. Hirudin was covalently crosslinked to the monoclonal antibody H18/7, which recognizes the extracellular domain of E-selectin, a normally silent, but cytokine-inducible, endothelial-leukocyte adhesion molecule. This immunoconjugate selectively bound to interleukin-1 (IL-1) activated, but not unactivated, cultured human umbilical vein endothelial cells (HUVEC) with a temporal profile similar to that of inducible cell surface procoagulant (tissue factor) activity. When bound to activated endothelial cells, the immunoconjugate significantly inhibited endogenous thrombin activity generated from coincubated human plasma, as well as fibrin clot formation on the monolayer surface. Intracellular processes mediated via the thrombin receptors such as ionized calcium mobilization and increases in cytoskeletal F-actin content, also were significantly down-regulated in activated endothelial cells treated with the hirudin immunoconjugate. The ability to selectively antagonize thrombin-dependent responses at the endothelial-blood interface may provide new insights into complex pathophysiological processes such as thrombosis and inflammation. This example also demonstrates the general feasibility of selective targeting of therapeutic agents to endothelial cells based on an activation-dependent surface phenotype.

Introduction

Activation of cultured human endothelial cells by inflammatory cytokines, such as IL-1 and TNF, or gram-negative bacterial endotoxin, leads to a transient procoagulant state that is due, in part, to the surface expression of tissue factor (Bevilacqua et al., *J. Exp. Med.* 160:618–623 (1984); Bevilacqua et al., *Am. J. Path.* 121:395–403 (1985)). This procoagulant activity can interact with plasma components to form a prothrombinase complex that cleaves prothrombin to generate thrombin (Nemerson, Y., *Blood* 71:1–8 (1988); Rapaport, S. I., *Adv. Exp. Med. Biol.* 281:97–103 (1990)). Thrombin generation at the vessel-wall interface, in vivo, is predicted to be an important component of the pathophysiology of various disease processes.

To further investigate the role of thrombin in vascular response-to-injury processes, such as intimation, wound-healing, arterial hyperplasia and atherogenesis, the present inventor attempted to modulate the actions of thrombin at the blood-vessel wall interface by selectively targeting the natural thrombin inhibitor, hirudin, to the surface of activated endothelial cells. For this purpose, an immunoconjugate composed of hirudin chemically crosslinked to the E-selectin-specific monoclonal antibody H18/7 (Bevilacqua et al., *Proc. Natl. Acad. Sci. USA* 84:9238–9242 (1987)) was constructed. E-selectin (CD62E) was chosen as the targeted activation antigen because it typically is not expressed in unactivated endothelial cells, but upon activation by cytokines and bacterial endotoxin, is abundantly expressed on the cell surface with a similar temporal pattern of induction as tissue factor (Pober et al., *J. Immunol.* 136:1680–1687 (1986); Bevilacqua and Gimbrone, *Seminars in Thrombosis and Hemostasis* 13:425–433 (1987)). Both molecules are products of activation-dependent genes, with peak cell surface expression in cultured human endothelial cells typically occurring at 4–6 hours, followed by a rapid return to near-background levels by 24 hours.

Hirudin, a highly specific and potent direct-acting inhibitor of thrombin, is an approximately 10,000 MW protein produced in the salivary gland of the leach, *Hirudo medicinalis*. Hirudin forms a high affinity complex with thrombin by binding to its anion binding exosite, thereby blocking the ability of thrombin to cleave fibrinogen, and also to activate its receptor (Stone and Maraganore, "Hirudin interactions with thrombin" in Berliner, L. ed., *Thrombin: Structure/Function*, Plenum Press, New York (1992), pp. 92–104; Rydel et al., *Science* 249:277–280 (1990)). It was reasoned that successful targeting of this inhibitor would permit the evaluation of the contribution of thrombin to pathophysiologic processes occurring in the vicinity of the activated endothelial cell surface.

Materials and Methods

Cells and Reagents:

Human endothelial cells were isolated from segments of pooled normal term umbilical cord veins, and cultured in Medium 199 (BioWhittaker, Walkersville, Md.) supplemented with 20% fetal bovine serum (FBS) (Hyclone, Logan, Utah), endothelial mitogen 50 µg/mL (Biomedical Technologies, Inc., Stoughton, Mass.), penicillin 100 units/mL and streptomycin 100 µg/mL (BioWhittaker, Walkersville, Md.), as described previously (Luscinskas et al., *J. Immunol.* 146:1617–1625 (1991)). For experimental use, human umbilical vein endothelial cells (HUVEC) were plated at the second subculture in culture wells coated with 0.1% gelatin (DIFCO, Detroit, Mich.). The murine monoclonal antibody H18/7 ($IgG_{2a}$) recognizes a functional epitope on human E-selectin (Bevilacqua et al., *Proc. Natl. Acad. Sci. USA* 84:9238–9242 (1987); Bevilacqua et al., *Science* 243:1160–1165 (1989)), while Rb1/9 ($IgG_1$ recognizes rabbit VCAM-1 (but not its human homologue) (Cybulsky et al., *Science* 251:788–791 (1991)). Recombinant desulfato-hirudin was obtained from Ciba-Geigy (Basal, Switzerland). The crosslinker N-succinimidyl 3-(2-pyridyldithio) propionate (SPDP) was purchased from Pierce Chemical (Rockford, Ill.). The chromogenic substrate, Spectrozyme TH, was purchased from American Diagnostica Inc. (Greenwich, Conn.). Purified human thrombin was purchased from Haematologic Technologies, Inc. (Essex Junction, Vt.). Purified recombinant human interleukin-1 beta (rhIL-1β) was a gift from Biogen (Boston, Mass.). Rhodamine phalloidin was purchased from Molecular Probes (Eugene, Oreg.). Whole blood was drawn from normal human volunteers into collection tubes containing a solution of 1:9 100 mM sodium citrate and 136 mM dextrose, pH 6.5. Plasma was isolated after centrifugation (700×g) for 5 minutes, then depleted of platelets by a 2 minute microcentrifuge spin (16,000×g). Dulbecco's phosphate buffered saline (DPBS), which contains 1.1 mM $Ca^{+2}$ and 0.5 mM $Mg^{+2}$, was purchased from BioWhittaker (Walkersville, Md.).

Crosslinking of Monoclonal Antibody H18/7 to Hirudin:

Recombinant hirudin was crosslinked to purified immunoglobulin of the monoclonal anti-E-selectin antibody H18/7 ($IgG_{2a}$), using the heterobifunctional crosslinker SPDP. Adapting the manufacturer's suggested protocol, 2-pyridyl disulfide groups were added to the hirudin by incubating 10 mg hirudin dissolved in 1.0 mL borate buffered saline (pH 9.0) with 20 µl SPDP (20 mM in DMSO), and to the purified immunoglobulin by incubating 25 mg IgG in 1.5 mL of the borate buffer with 200 µl of the 20 mM SPDP. The hirudin-bound PDP disulfide bonds were specifically reduced with 12 mg of dithiothreitol to expose thiol groups. The thiolated hirudin was incubated with the PDP derivatized IgG overnight in DPBS to allow crosslinking to occur. Free hirudin was then removed by gel filtration in DPBS on a G-75 Sephadex sizing column, and the immunoconjugate concentrated by centrifugation using a Centricon-30 microconcentrator (Amicon, Beverly, Mass.).

Immunoreactivity of the crosslinked preparation was evaluated by measuring binding to unactivated or IL-1 activated HUVEC monolayers using standard techniques in a quantitative fluorescence immunobinding assay, and compared with uncoupled H18/7 monoclonal antibody. The ability of the hirudin immunoconjugate to inhibit the activity of a known concentration of thrombin was also measured in a chromogenic assay and compared to a standard inhibition curve for free hirudin (see below).

Assay for Thrombin Activity:

Thrombin activity was quantitated in a microtiter plate with an amidolytic assay using a thrombin specific chromogenic substrate, Spectrozyme TH. Cleavage of Spectrozyme releases paranitroaniline, which can be quantitated by measuring an increase in absorbance at 405 nm. A source of thrombin, either diluted fresh human plasma incubated with activated endothelial cells (endogenous source), or purified human thrombin (exogenous source) in DPBS, was incubated with Spectrozyme TH substrate for 15–30 minutes at 37° C. in a water bath and the assay stopped by the addition of glacial acetic acid. Thrombin enzymatic activity, which was linear over this time range, was determined by measuring cleaved substrate spectrophotometrically, using a microplate reader (Biorad model 3550). In certain assays, varying concentrations of recombinant hirudin were added to the incubation mixture and the resulting inhibition of thrombin activity measured.

Generation of Thrombin by Activated Endothelial Cell Cultures:

HUVEC monolayers cultured in microtiter wells were activated by incubation for 4 hours with rhIL-1β (10 U/mL). Monoloyers were washed once with DPBS and then incubated at 37° C. in 100 µl DPBS with 2x final concentration of human platelet-poor plasma and 100 µl of the chromogenic substrate. The amount of cleaved substrate was determined by measuring the $OD_{405}$ in a microplate reader. Thrombin activity could be detected within 15 minutes and was linear over 30 minutes. At least 1% plasma was required to generate a detectable level of thrombin activity. At 10% plasma, thrombin activity was also generated at detectable levels with unactivated HUVEC monolayers. Therefore, 1% plasma was routinely used for this assay. In assays testing the effect of the immunoconjugate, H18/7-hirudin (100 µg/mL), in RPMI with 1% FBS, was incubated with the activated endothelial monolayer on ice for 30 minutes. The unbound hirudin immunoconjugate was washed out prior to the addition of plasma and the chromogenic substrate.

Plasma Clotting Assay on Activated Endothelial Cell Cultures:

Clot formation on the surface of intact IL-1 activated HUVEC was measured in a plasma recalcification assay, using a microplate reader to detect an increase in opacity over time as plasma fibrinogen was converted to fibrin (Chang et al., *Thrombosis Research* 66:599–602 (1992)). Confluent HUVEC monolayers in microtiter wells were activated with rhIL-1β for 4 hours at 37° C., then incubated with control antibody or hirudin-H18/7 immunoconjugate (1 mg/mL) for 30 minutes on ice, and washed three times with Tris buffer (0.02M Tris in 0.15M NaCl, pH 7.2) prior to assay. Citrated platelet-poor plasma was added in combination with Tris buffer to yield final assay concentrations ranging from 1 to 10% whole plasma. In some cases, varying concentrations of hirudin were also added. Clotting was initiated by recalcification with $CaCl_2$ (12.5 mM final concentration). The plates were incubated at room temperature, and the $OD_{405}$ measured at selected times.

Quantitation of F-actin in Endothelial Monolayers:

The F-actin content of HUVEC was quantitated, essentially as described previously (Thurston et al., supra). Briefly, after activation with rhIL-1β (10 U/mL, 4 hour), replicate confluent monolayers in microtiter wells were washed, incubated on ice for 30 minutes with the hirudin-immunoconjugate. The monolayers were then washed four times with DPBS containing 0.5% BSA, and incubated for 15 minutes at 37° C. with diluted human plasma (as an endogenous thrombin source) or purified human thrombin in DPBS-BSA buffer. The monolayers were then fixed with 3.7% formaldehyde in DPBS for 5 minutes at room temperature, washed three times, permeabilized with a buffer containing 1.4% formaldehyde in DPBS and 0.1% NP-40 for 90 seconds at room temperature, and stained with rhodamine-phalloidin (1:10 in DPBS) for 40 minutes at room temperature. After three additional washes, 100 µl of methanol was added to each well, and F-actin content was measured using a microplate fluorescence reader (Pandex) with an excitation wavelength of 545 nm and an emission wavelength of 575 nm.

Microscopic Evaluation of Monolayer Integrity:

In certain experiments, monolayer integrity was evaluated morphologically by phase contrast and immunofluorescence microscopy. For this purpose, HUVEC were grown to confluence on gelatin-coated (0.1%) Permanox Lab-Tek chamber slides (Nunc, Naperville, Ill.), and fixed with 3.7% formaldehyde in DPBS for 40 minutes at room temperature, following plasma co-incubation or thrombin treatment, with and without hirudin-immunoconjugate pretreatment. To visualize the organization of the cytoskeleton, staining of permeabilized monolayers with rhodamine-phalloidin was carried out as described above.

RESULTS

Hirudin Immunoconjugate Exhibits Antithrombin Activity

Figure 3A:
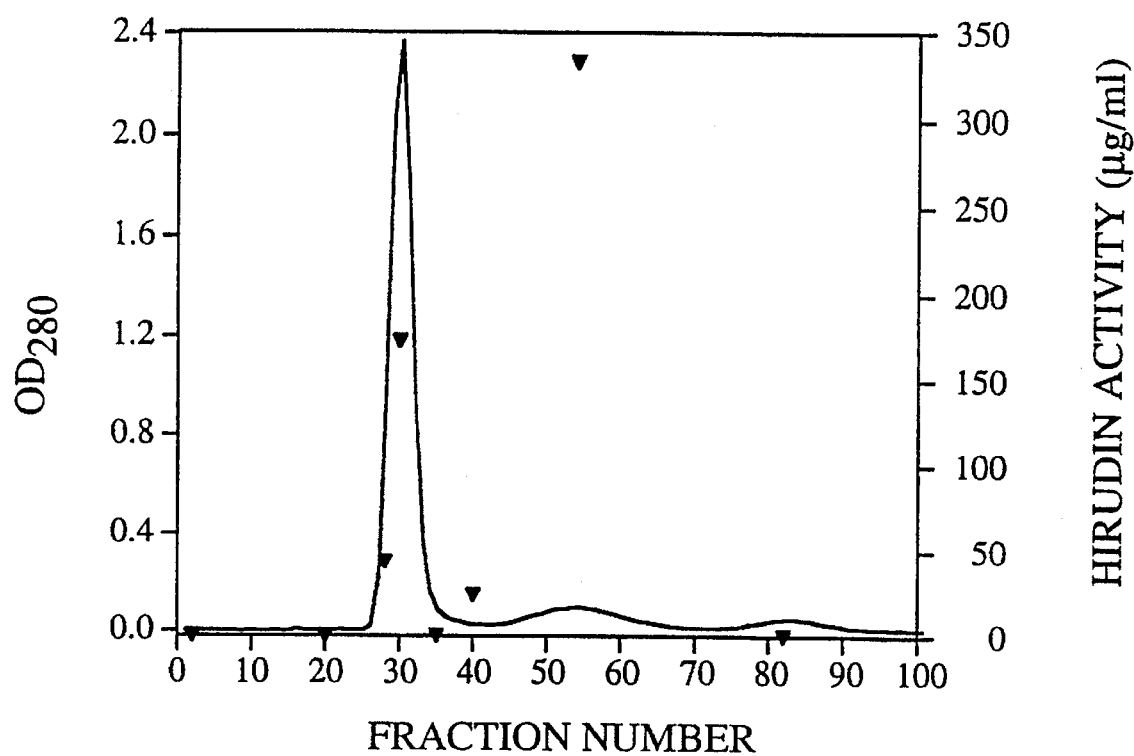
FIG. 3A depicts a gel chromatographic separation of H18/7 IgG-hirudin immunoconjugate from free hirudin on Sephadex G-75. Following the crosslinking reaction, free hirudin was removed from the mixture by applying the sample (2–3 mL) to a Sephadex G-75 column (1.5×40 cm) using DPBS buffer. One mL fractions were collected and $OD_{280}$ recorded (solid line). Hirudin (anti-thrombin) activity of selected fractions was quantitated (closed triangles) using the Spectrozyme chromogenic assay. Precalibration of the column showed elution of unconjugated IgG in fractions 28–32 (void volume) and free hirudin (standard) in a broad peak spanning fractions 45–62. Data represent mean values from one of eight similar preparations.
Figure 3B:
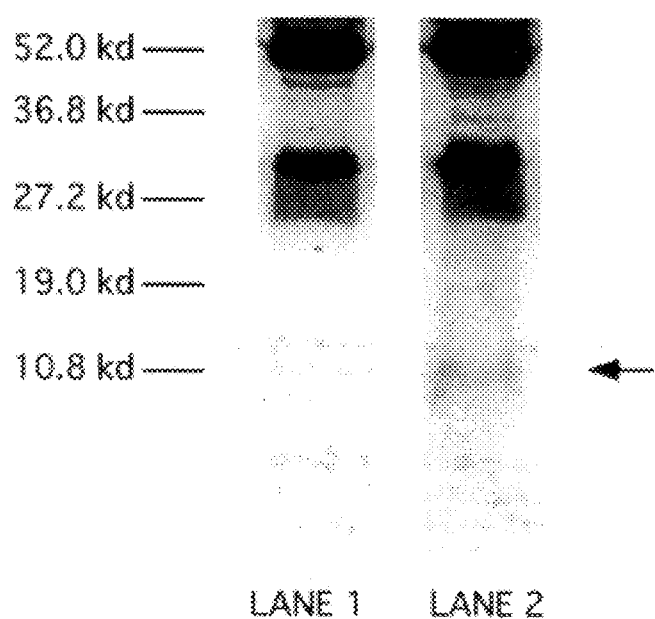
FIG. 3B depicts an SDS-PAGE electrophoretic analysis of void volume activity peak. Pooled fractions 28–32 were analyzed by SDS-PAGE (4–15%) under reducing conditions. Lane 1, unconjugated H18/7 IgG; Lane 2, immunoconjugate. Note the presence of released hirudin (arrow) in the reduced immunoconjugate sample.

After the crosslinking procedure, free hirudin was separated from the crosslinked compound (and any unreacted immunoglobulin) by gel filtration on a G-75 sizing column (1.5×40 cm) (FIG. 3A). Selected fractions were tested for hirudin (anti-thrombin) activity using the Spectrozyme chromogenic assay. The hirudin activity of the test samples was quantified by comparison to known amounts of uncoupled hirudin required to neutralize a human thrombin standard. The bulk of the hirudin activity was found in the low molecular weight fractions corresponding to free hirudin. Significant hirudin activity, however, was recovered in the IgG-containing void volume. When this peak was rechromatographed, the hirudin activity again remained in the void volume. This void volume activity peak was evaluated on 4–15% SDS-PAGE. Under nonreducing conditions, only one band was seen at approximately 150 kd. Under reducing conditions, 3 bands appeared: 50 kd (IgG heavy chain), 25 kd (IgG light chain), and a 10 kd band (free hirudin) (FIG. 3B). Eight separate H18/7-hirudin conjugates were prepared, the anti-thrombin activities of which ranged from 27 to 115 µg activity per mg protein, corresponding to an average specific activity of roughly 1 molecule of hirudin per molecule of IgG. At least two different preparations of immunoconjugate were utilized in each of the experimental studies described below.

Hirudin Immunoconjugate Retains Selective Immunoreactivity

Figure 4A:
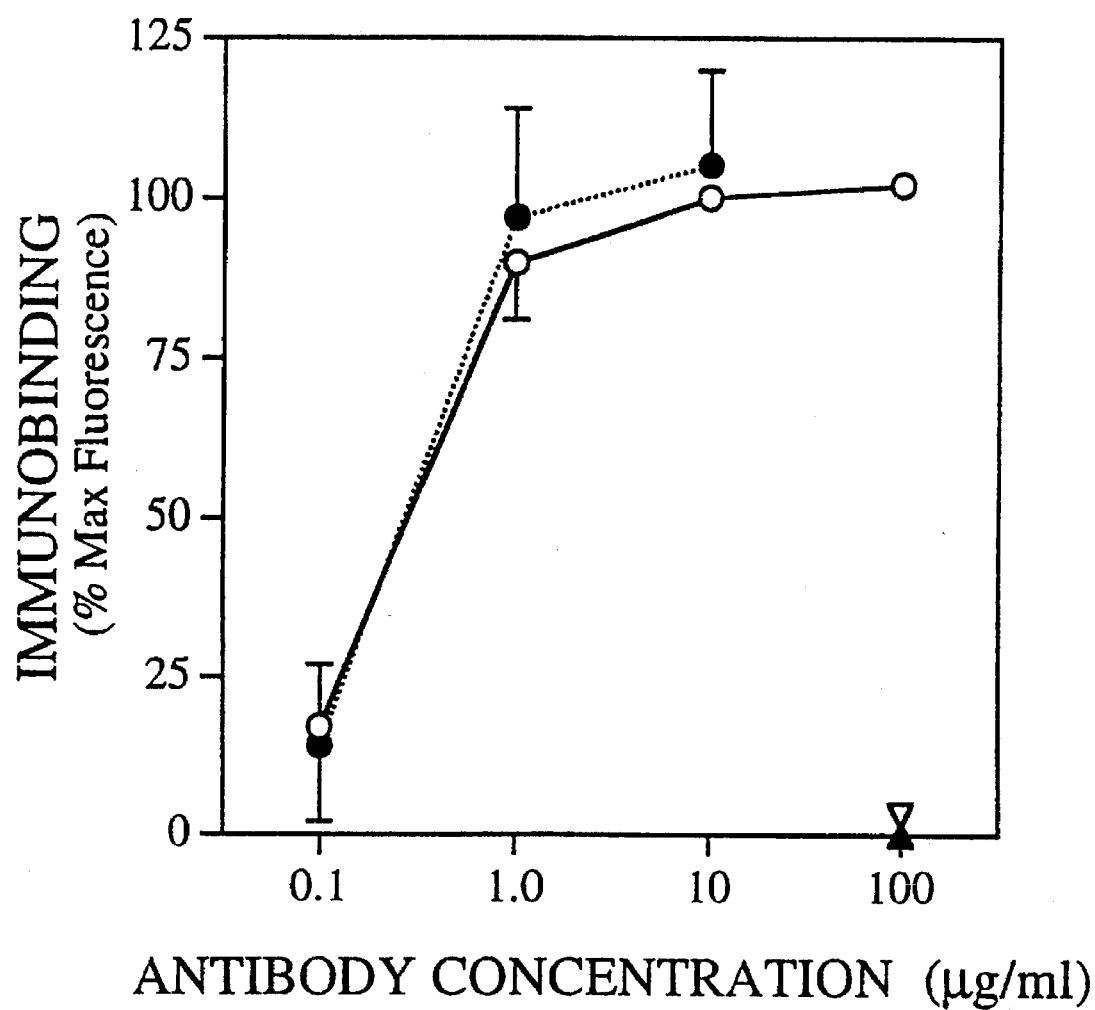
FIG. 4A is a graph depicting the activation-dependent binding of H18/7-hirudin immunoconjugate to HUVEC monolayers. This graph demonstrates that H18/7-hirudin immunoconjugate and unreacted H18/7 IgG have comparable immunobinding reactivity with HUVEC monolayers. Increasing concentrations of H18/7 IgG (open circles) or H18/7-hirudin immunoconjugate (closed circles) were incubated with rhIL-1β activated (10 U/mL, 4 hours) HUVEC for 30 minutes on ice. Unbound antibody was then washed out and FITC-conjugated goat anti-mouse IgG was added. After incubation on ice for 30 minutes, wells were washed and fluorescence quantitated in a fluorescence microplate reader. Immunobinding data are presented as mean (±standard deviation) percent maximum fluorescence from five separate experiments with triplicate determinations in each. Triangles (open, H18/7; closed, H18/7-hirudin) illustrate binding to unactivated HUVEC, at highest concentration of reagent tested (100 μg/mL).
Figure 4B:
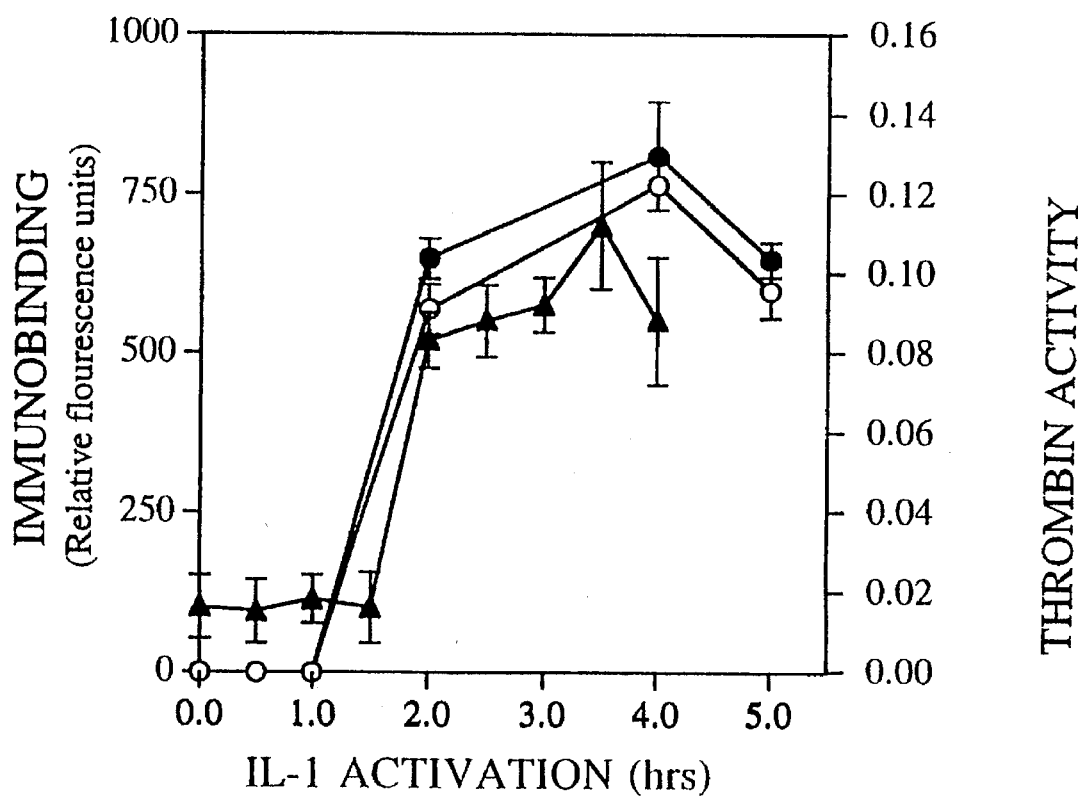
FIG. 4B is a graph demonstrating that a temporal pattern of E-selectin expression on activated HUVEC is similar to that of inducible thrombin-generating activity. HUVEC activated with rhIL-1β (10 U/mL) for different times were tested for binding of H18/7 IgG (open circles) or H18/7-hirudin immunoconjugate (closed circles) (1 μg/mL, each reagent). At the same time, the thrombin activity (closed triangles) generated from 1% human platelet-poor plasma incubated with these activated monolayers was measured ($OD_{450}$, Spectrozyme chromogenic assay). After 4 hours, the activity generated by activated HUVEC monolayers from 1% plasma was equal to that of 1 Unit/mL purified human thrombin. The data (mean ±standard deviation, triplicate determinations) illustrated are from 1 of 3 similar experiments.

The crosslinking procedure did not affect the ability of the E-selectin antibody to interact with the surface of cytokine activated HUVEC, as demonstrated in a quantitative immunobinding assay (FIG. 4A). When preparations of the H18/7-hirudin immunoconjugate was compared with uncoupled H18/7 IgG, equivalent, dose-dependent, saturable binding to IL-1 activated HUVEC monolayers was observed, with maximum binding achieved above 1.0 µg/mL of added antibody. Neither the immunoconjugate nor uncoupled IgG bound delectably to unactivated HUVEC. Binding of both compounds was detected within two hours of IL-1 activation, with maximum levels seen by four hours (FIG. 4B). This was consistent with the previously reported temporal pattern of inducible E-selectin surface expression in this cell system (Bevilacqua et al., Proc. Natl. Acad. Sci. USA 84:9238–9242 (1987)).

Hirudin Immunoconjugate Inhibits Thrombin Generation from Plasma

Figure 5A:
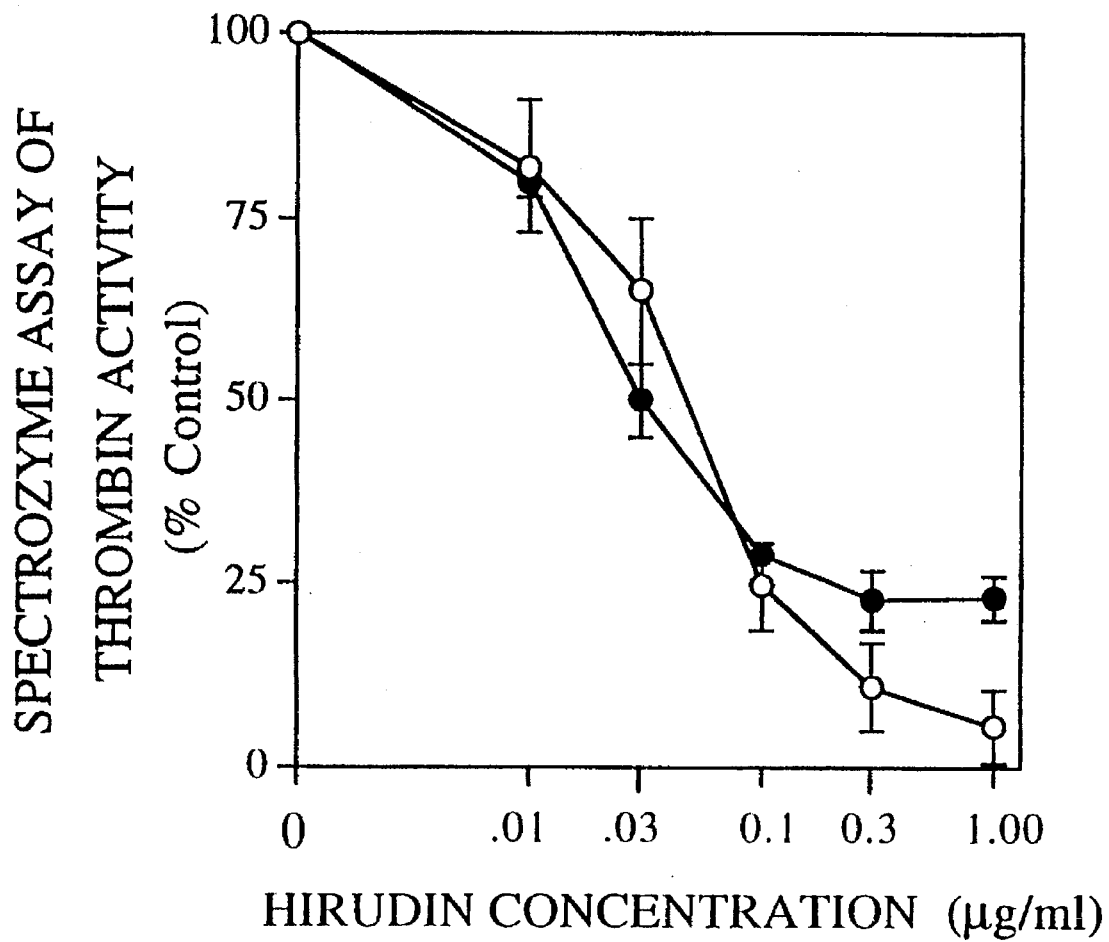
FIG. 5A is a graph depicting dose-dependent inhibition by unconjugated hirudin of exogenous thrombin and endogenous thrombin activity generated from plasma in contact with activated HUVEC. Human thrombin (1 Unit/mL) (open circles) or 1% human plasma (closed circles) was incubated with recombinant hirudin and Spectrozyme chromogenic substrate in the presence of rhIL-1β activated (10 U/mL, 4 hours) HUVEC monolayers. The data (mean ±standard deviation, triplicate determinations) illustrated are from 1 of 3 similar experiments.
Figure 5B:
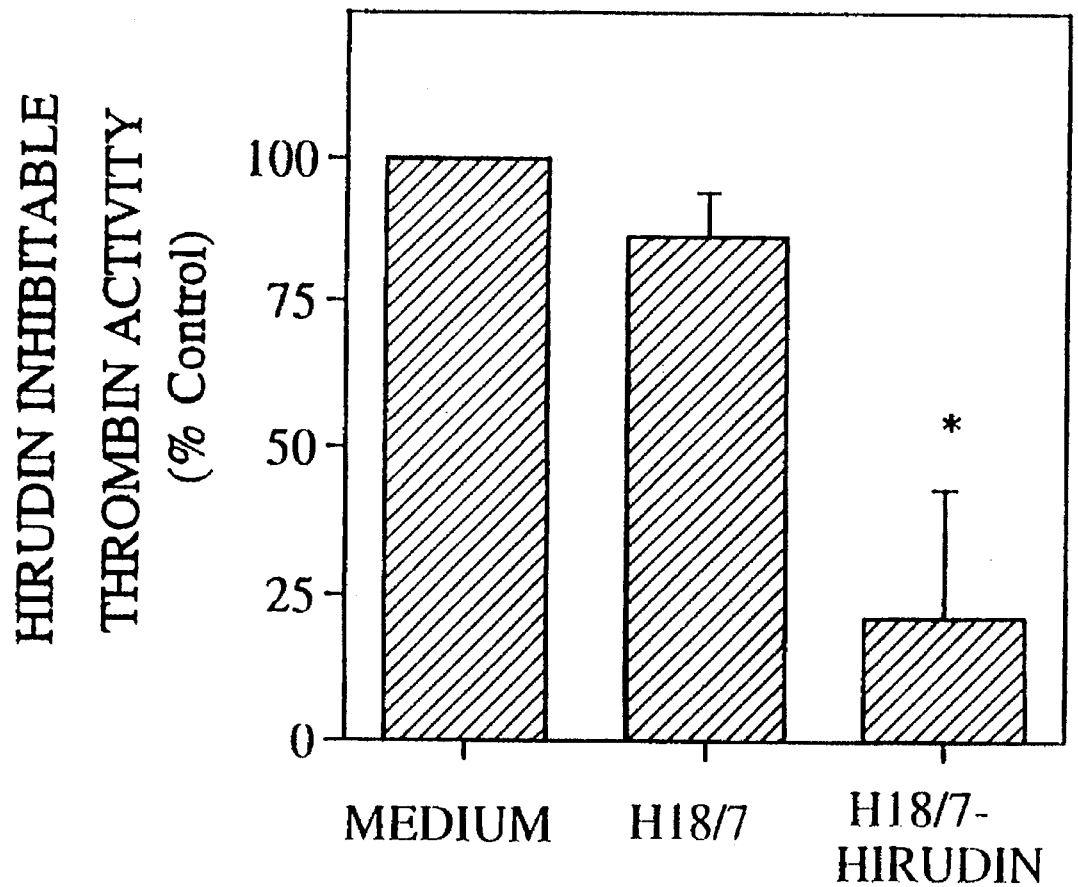
FIG. 5B is a bar graph depicting the inhibition of endogenous thrombin activity by hirudin immunoconjugate. HUVEC monolayers, activated as above, were treated with H18/7 IgG or the H18/7-hirudin immunoconjugate (100 µg/mL). After unbound antibody was removed, a Spectrozyme assay was performed to assess endogenous thrombin activity generated from 1% human plasma. Results are presented as (unconjugated) hirudin-inhibitable thrombin activity (mean ±standard deviation) from 3 separate experiments with triplicate determinations in each. The * in the figure indicates significant inhibition (p<0.05) versus medium control (no antibody added) using a two-tailed Student's t-test.

Cytokine and/or endotoxin activation of HUVEC results in the induction and surface expression of tissue factor activity, and renders these cultured endothelial monolayers prothrombotic (Bevilacqua et al., J. Exp. Med. 160:618–623 (1984); Bevilacqua et al., Am. J. Path. 121:395–403 (1985); Bevilacqua and Gimbrone, Seminars in Thrombosis and Hemostasis 13:425–433 (1987)). When HUVEC monolayers were treated with rhIL-1β, the capability of generating thrombin activity from added human plasma developed in a similar temporal pattern as inducible H18/7 immunobinding (E-selectin cell surface expression) (FIG. 4B). Based on a comparison of dose-response curves for free hirudin inhibition of an exogenous thrombin standard, the amount of endogenous thrombin activity generated from 1% human platelet-poor plasma in this cell system was on the order of magnitude of 1 unit/mL (FIG. 5A). In three separate experiments utilizing two different preparations of the hirudin immunoconjugate, significant (79%+/−22%, p<0.05) inhibition of plasma-generated thrombin activity was observed (FIG. 5B). In contrast, treatment with uncoupled H18/7 IgG did not have any inhibitory effect. When free hirudin was pre-incubated in parallel with activated HUVEC monolayers and then washed out before the addition of plasma, no residual inhibition of endogenously generated thrombin activity was seen.

Hirudin Immunoconjugate Delays Plasma Clotting Time

Figure 6:
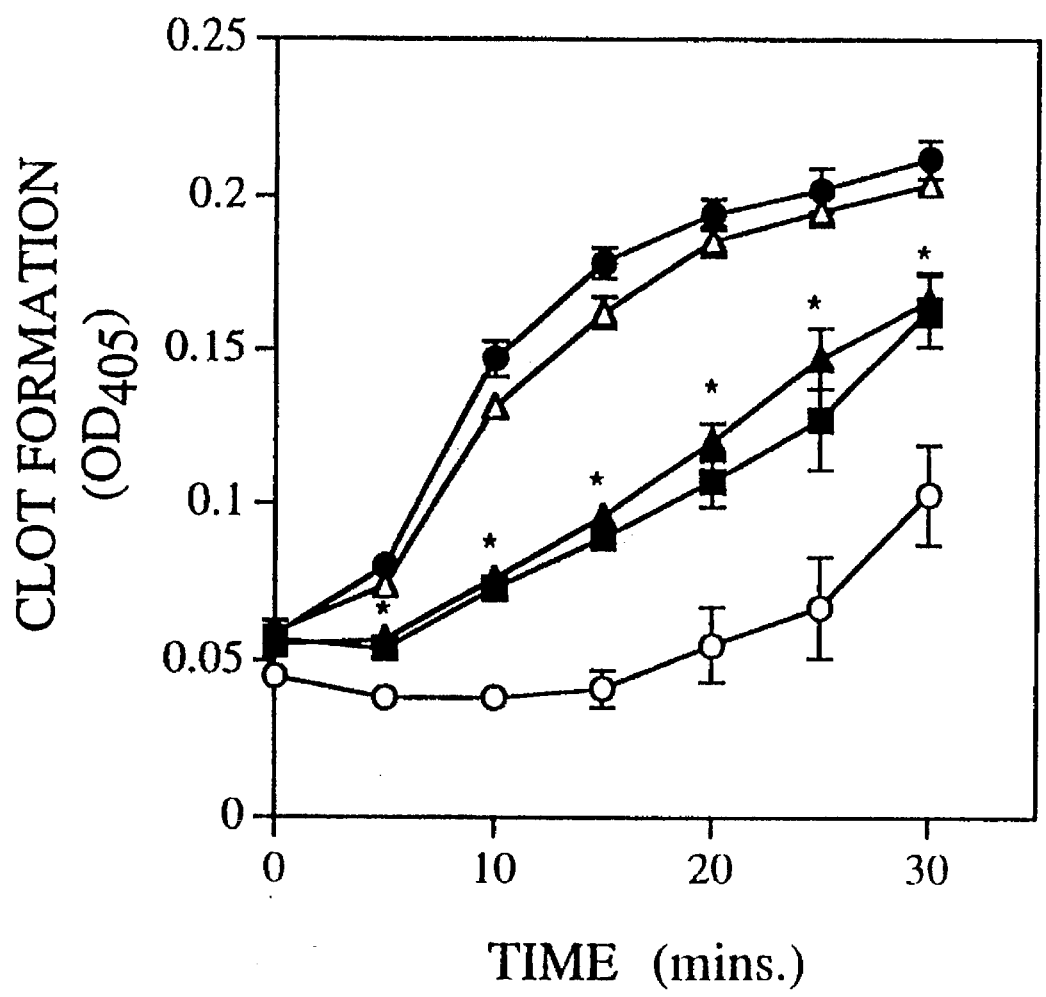
FIG. 6 is a graph demonstrating that the hirudin-H18/7 immunoconjugate selectivity inhibits plasma clot formation on activated HUVEC monolayers. Activated (rhIL-1β, 10 U/mL, 4 hours) HUVEC monolayers, in microtiter plates, were pretreated with either H18/7-hirudin immunoconjugate (closed triangles), uncoupled H18/7 IgG (open triangles), or no antibody (closed circles). Fresh citrated human plasma (10%) was then added to each microtiter well and fibrin generation measured (as increased opacity, $OD_{405}$) at intervals after recalcification. The effect of free hirudin (0.1 µg/mL, closed squares), and the time course of clot formation on unactivated endothelium (open circles) are also illustrated for comparison. The results are presented as mean (±standard deviation) from 1 of 3 similar experiments done in triplicate. The * in the figure indicates significant inhibition (p<0.005) versus control (no antibody added) using a two-tailed Student's t-test.

Clot formation was detected in a plasma recalcification assay performed on HUVEC monolayers in microtiter wells. In this in vitro model system, IL-1 activated HUVEC monolayers serve as a source of cell-surface available tissue factor activity that initiates the coagulation cascade in the coincubated plasma, thus generating thrombin, which then cleaves fibrinogen to form fibrin. In preliminary experiments, when 10% human plasma was added to the activated endothelial monolayers and recalcified, a change in optical density due to fibrin generation was detected at 10 minutes and was maximal at 30 minutes. Within this time interval, free (uncoupled) hirudin inhibited plasma clot formation over a broad concentration range, in a dose-dependent manner, with virtually complete inhibition observed at 1.0 µg/mL added hirudin. In three separate experiments, pretreatment with the hirudin-H18/7 immunoconjugate resulted in significant (p<0.005) inhibition of clot formation (ranging from 22 to 49%) at all time points examined, from 5 to 30 minutes (FIG. 6). The level of inhibition observed with the H18/7-hirudin immunoconjugate was comparable to that obtained, in parallel assays, with 0.1 μg/mL free hirudin. When preparations of hirudin crosslinked to the non-binding murine monoclonal antibody Rb 1/9 (anti-rabbit VCAM-1) were substituted for the H18/7 immunoconjugate, no decrease in clot formation was observed (not shown). Over time, inhibition of clot formation by either free hirudin or the cell surface-bound hirudin-immunoconjugate was overcome, presumably because of the redundant and cascading nature of the coagulation process. At later time points, clot formation was detectable on unactivated endothelial monolayers (FIG. 6). When hirudin crosslinked to a non-binding antibody (Rb1/9, anti-rabbit VCAM-1) was used, there was no delay in clot formation.

Figure 7:
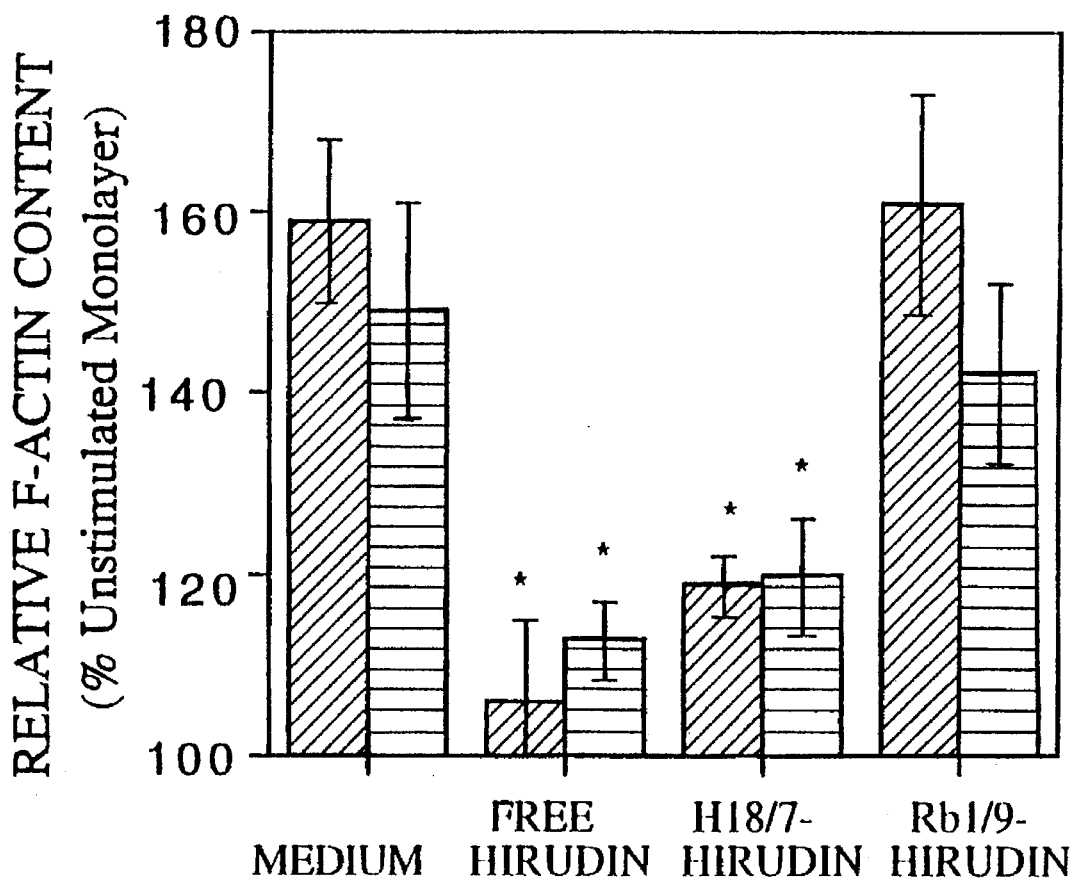
FIG. 7 is a bar graph demonstrating that immunotargeted hirudin inhibits thrombin-induced increases in F-actin content in HUVEC monolayers. Activated (rhIL-1β, 10 U/mL, 4 hours) HUVEC monolayers were treated with 0.1 Unit/mL human thrombin (horizontal crosshatched bars), or 2% platelet-poor human plasma (diagonal crosshatched bars) for 15 minutes, and relative F-actin content was measured by labelling fixed, permeabilized cells with rhodamine phalloidin. Experimental pretreatments included: control medium, unconjugated (free) hirudin (0.1 µg/mL), and H18/7-hirudin (activation-specific binding), or Rb1/9-hirudin (non-binding) immunoconjugates. F-actin content was normalized to that of unstimulated unactivated HUVEC monolayers (100%). Results shown are the mean values (±standard deviation) of 3 separate experiments, performed in triplicate. The * in the figure indicates a significant difference (p<0.05) from the corresponding control using a two-tailed Student's t-test.

Hirudin Immunoconjugate Inhibits Thrombin Induced Increases in F-Actin Content and Promotes Monolayer Integrity In in vitro model systems (Sago et al., *Thrombosis and Haemostasis* 67:331–334 (1992); Garcia et al., *J. Cell. Physiol.* 128:96–104 (1986)), thrombin has been reported to induce endothelial cell shape change and alterations in endothelial monolayer permeability to macromolecules, presumably via activation of specific thrombin receptors. Both of these effects are accompanied by dramatic changes in the organization of the cytoskeleton, in particular, actin micro filaments (Thurston et al., *Microvascular Research* 47:1–20 (1994)). In preliminary experiments, the F-actin content of both unactivated and IL-1 activated HUVEC monolayers, as measured by rhodamine-phalloidin binding, was detectably increased by the addition of as little as 0.03 Unit/mL of purified human thrombin. The addition of human plasma (2%, recalcified) to HUVEC monolayers also caused an increase in F-actin content (comparable to the maximal stimulation obtained with 0.1 Unit/mL of exogenous thrombin) (FIG. 7), but only if the monolayers were cytokine-activated (IL-1, 10 U/mL, 4 hours) to allow endogenous thrombin generation to occur. In three separate experiments, thrombin-induced increases in HUVEC F-actin content were significantly antagonized by the addition of uncoupled hirudin (0.1 μg/mL) (90+/-9% inhibition, exogenous thrombin; 74+/-4% inhibition, plasma-generated thrombin activity), or the specifically bound hirudin-H18/7 immunoconjugate (60+/-6% and 68+/-3% inhibition, respectively), but not the non-binding (control) hirudin-Rb1/9 immunoconjugate (FIG. 7).

Figure 8A:
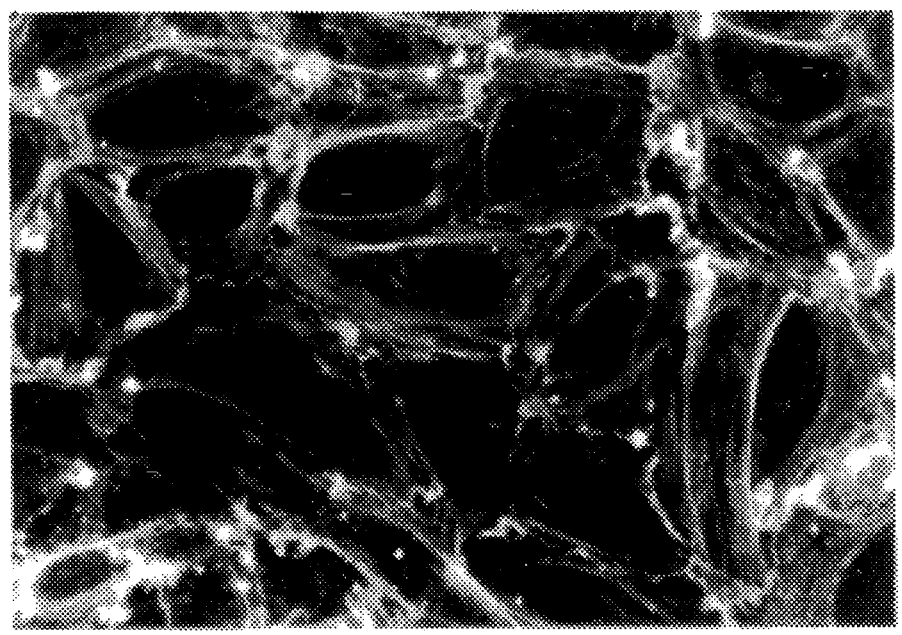
FIG. 8A is a photograph of a fluorescently stained microscope slide of activated (rhIL-1β, 10 U/mL, 4 hours) confluent HUVEC monolayers treated with medium alone. After treatment, the monolayers were fixed, permeabilized, and stained with rhodamine phalloidin and examined by fluorescence microscopy. The photograph of FIG. 8A depicts confluent, intact endothelial monolayer.
Figure 8B:
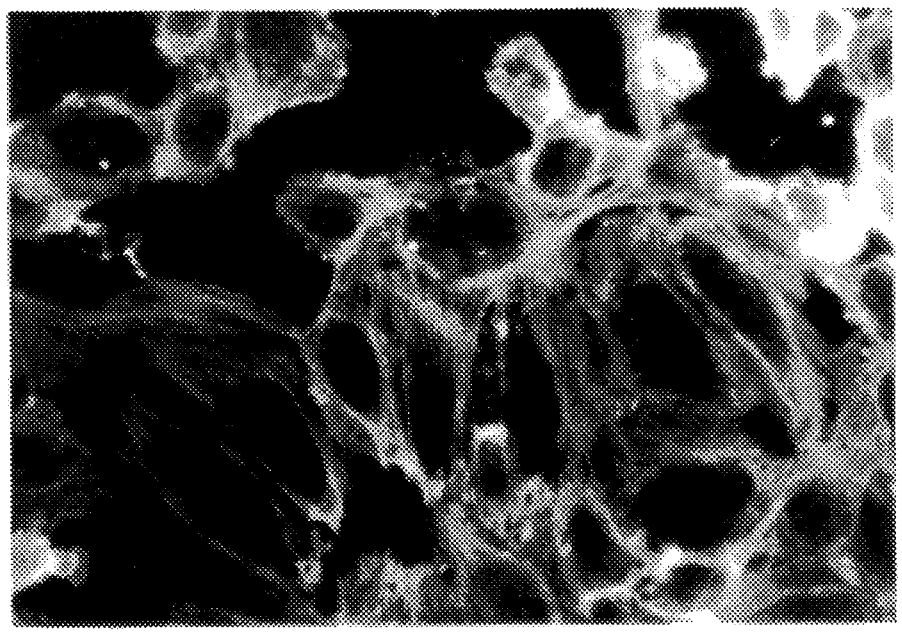
FIG. 8B is a photograph of a fluorescently stained microscope slide of activated confluent HUVEC monolayers treated with medium containing 2% recalcified human plasma for 15 minutes at 37° C. After treatment, the monolayers were fixed, permeabilized, and stained with rhodamine phalloidin and examined by fluorescence microscopy. The photograph of FIG. 8B depicts thrombin-induced disruption of the monolayer.
Figure 8C:
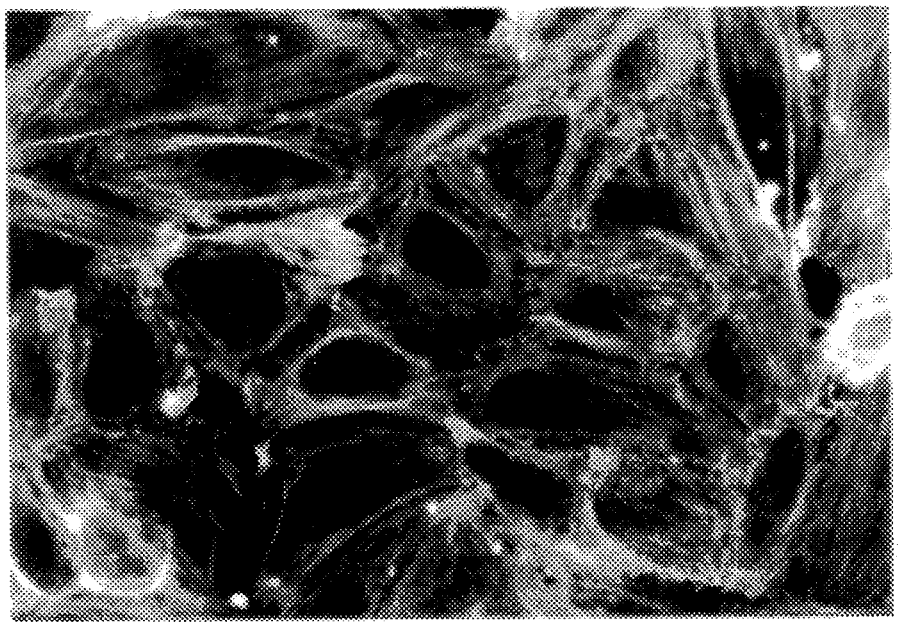
FIG. 8C is a photograph of a fluorescently stained microscope slide of activated confluent HUVEC monolayers treated with medium containing 2% recalcified human plasma for 15 minutes at 37° C. The monolayer was treated with the hirudin-H18/7 immunoconjugate (100 µg/mL) after IL-1 activation and prior to incubation with plasma. After treatment, the monolayers were fixed, permeabilized, and stained with rhodamine phalloidin and examined by fluorescence microscopy. The photograph of FIG. 8C depicts preservation of the intact monolayer by the immunoconjugate pretreatment.

Microscopic examination of confluent IL-1 activated HUVEC monolayers, after 15 minutes incubation with 2% recalcified human plasma, revealed cell retraction and disruption of monolayer integrity (FIGS. 8A,B). This response was inhibited by the addition of free hirudin suggesting that this resulted from the generation of endogenous thrombin in the vicinity of the procoagulant activated endothelial cell surface. Pretreatment with hirudin immunoconjugate, after IL-1 activation, but prior to incubation with plasma, essentially ablated this thrombin-induced effect (FIG. 8C).

DISCUSSION

E-selectin, an endothelial-specific, cytokine-inducible leukocyte adhesion molecule, is rapidly upregulated on the surface of cultured human vascular endothelial cells in a temporal profile that coincides with the expression of tissue factor procoagulant activity (Bevilacqua et al., *J. Exp. Med.* 160:618–623 (1984); Bevilacqua et al., *Proc. Natl. Acad. Sci. USA* 84:9238–9242 (1987); Bevilacqua and Gimbrone, *Seminars in Thrombosis and Hemostasis* 13:425–433 (1987)). Thus, coincubation of activated endothelial monolayers with human plasma would be predicted to result in the generation of thrombin activity at the endothelial cell surface in close proximity to the extracellular domains of E-selectin molecules. The present inventor has exploited these properties of the activated endothelial phenotype in the design of an immunoselectively targeted therapeutic agent to antagonize thrombin-dependent processes in a cell-specific and context-defined fashion.

Murine monoclonal antibody H18/7 is an adhesion-blocking, E-selectin-specific reagent that does not interact with unactivated human endothelial cells. Hirudin, a potent naturally occurring anticoagulant, forms a tight, highly stable, noncovalent complex with thrombin that blocks both its proteolytic cleavage of fibrinogen (and other substrates) and its ability to activate cellular receptors. Covalent crosslinking of these two components, using well established methodologies (Haber et al., *Science* 243:52–54 (1989)), yielded an immunoconjugate (FIGS. 3A and 3B) that retained appropriate immunoselectivity and antithrombin activity. This immunoconjugate preparation, like the unconjugated monoclonal antibody, exhibited dose-dependent, saturable binding to activated HUVEC monolayers, but failed to bind to unactivated HUVEC monolayers, thus satisfying the requirement of activation-dependent endothelial targeting (FIGS. 4A and 4B).

Although individual hirudin-H18/7 immunoconjugate preparations were not purified to homogeneity by the removal of unconjugated immunoglobulin, (which may account in part for variations in their anti-thrombin activity), all were effective in neutralizing both the exogenously added thrombin and endogenously generated thrombin, in the proximity of the activated endothelial surface (FIG. 5B). Based on an average coupling efficiency of 1 hirudin per IgG molecule (based on activity measurements), and an estimated density of $1 \times 10^6$ E-selectin molecules per cytokine-activated HUVEC (unpublished data), the calculated density of targeted hirudin molecules on the surface of a confluent monolayer ($1-2 \times 10^4$ cells per microliter well) would be on the order of $10-20 \times 10^{-15}$ moles per test well. Based on further comparisons with free hirudin and exogenous thrombin standard, the estimated concentration of thrombin generated by incubation of the activated endothelial monolayer with 1% human platelet-poor plasma is on the order of 1 Unit/mL (FIG. 5A). Thus, in multiple experiments, with different hirudin immunoconjugate preparations, these relatively small amounts of surface targeted hirudin exhibited antithrombin activities comparable to fluid-phase concentrations of free hirudin in the range of 10–30 nM (FIGS. 5A, 5B). The lack of effect of unconjugated H18/7 immunoglobulin or residual free hirudin (after sham addition and wash-out) confirmed that a selective targeting of the antithrombin immunoconjugate to the endothelial surface was, in fact, responsible for this observed inhibition (FIG. 5B).

Studies of the kinetics of clotting of recalcified human plasma on the activated endothelial surface provided further evidence of the efficacy of immunotargeted hirudin to antagonize thrombin-dependent interface reactions. Again, fmole amounts of surface-targeted hirudin immunoconjugate were equivalent to 10 nM fluid-phase concentrations of free hirudin in inhibiting the generation of fibrin in this in vitro model system (FIG. 6). This result is all the more striking, given the enzymatic amplification inherent in the coagulation cascade from the level of tissue factor activation to the endpoint of fibrin generation, and the absence of any fluid movement that might enhance thrombin-inhibitor complex formation at the monolayer surface.

Immunotargeting of hirudin was also effective in antagonizing certain intracellular effects of thrombin in cultured endothelial monolayers (FIGS. 7, 8A, 8B, 8C), presumably mediated via cell surface receptors (Coughlin et al., supra). The increases in F-actin content that accompany thrombin-induced reorganization of the endothelial cytoskeleton (Thurston et al., supra), mediated either by exogenous thrombin or by an endogenous (plasma) generating source (FIG. 7), were significantly inhibited by hirudin-H18/7 in an immunospecific fashion and to a degree comparable to free hirudin. Further, the striking cell retraction and monolayer disruption induced by plasma clotting and thrombin generation on the activated endothelial monolayer also was effectively antagonized by the hirudin-H18/7 conjugate (FIGS. 8A, 8B, 8C). Activation of thrombin receptors in vascular endothelial cells typically results in a transient rise in the levels of intracellular ionized calcium (Sago et al., Thrombosis and Haemostasis 67:331–334 (1992)); in preliminary experiments, hirudin-H18/7 immunoconjugate also significantly inhibited this thrombin-induced response, as measured in Fura-2-loaded HUVEC (unpublished observations). The ability to selectively inhibit these thrombin-mediated cellular events may provide pathogenetic insights into the endothelial dysfunction associated with acute inflammatory and thrombotic states in which thrombin generation at the blood-vessel wall interface is occurring (Bevilacqua et al., Am. J. Path. 121:395–403 (1985); Daniel et al., J. Biol. Chem. 261:9579–9582 (1986); Zimmerman et al., Ann. N.Y. Acad. Sci. 485:349–368 (1986); Jaffe et al., J. Biol. Chem. 262:8557–8565 (1987); Sporn et al, Cell 46:185–190 (1986); Gimbrone, M. A., "Vascular endothelium in health and disease" in Molecular Cardiovascular Medicine, Haber, E. ed., Scientific American Medicine, New York (1994) (in press); Nelken et al., J. Clin. Invest. 90:1614–1621 (1992)).

In conclusion, it has been demonstrated that the immunoselective targeting of the antithrombin agent hirudin to the surface of human endothelial cells, in an activation-dependent fashion, can significantly reduce the thrombogenicity of this interface, as well as modify thrombin-mediated cellular events. This approach, applied in appropriate in vitro and in vivo models, provides a useful tool to probe the multiple roles of thrombin as a pleiotropic mediator in vascular pathophysiology. In addition, the principle of activation-dependent immunotargeting to vascular endothelium in vivo can be used to selectively target appropriate therapeutic agents to sites of activated endothelium. This concept could also be extended to other therapeutic interventions (e.g., antioxidant, anti-adhesive, anti-complement, and immunosuppressive agents) in various disease settings (e.g., acute and chronic inflammation, vasculitis, sepsis, transplant rejection, atherosclerosis) in which endothelial activation plays a role (Cybulsky et al., Science 251:788–791 (1991); Gimbrone, M. A., "Vascular endothelium in health and disease" in Molecular Cardiovascular Medicine, Haber, E. ed., Scientific American Medicine, New York (1994) (in press); Drake et al., Amer. J. Pathol. 142:1458–1470 (1993); Briscoe et al., "Predictive Value of Inducible Endothelial Cell Adhesion Molecule Expression for Acute Rejection of Human Cardiac Allografts," Transplantation (1995) (in press)).

All publications and patent applications mentioned in this specification are indicative of the level of skill of those skilled in the art to which this invention pertains. All publications and patent applications are herein incorporated by reference to the same extent as if each individual publication or patent application were specifically and individually indicated to be incorporated by reference.

Having now fully described this invention, it will be understood by those of skill in the art that the same can be performed within a wide and equivalent range of conditions, formulations, and other parameters without affecting the spirit or scope of the invention or any embodiment thereof.

What is claimed is:

1. A method for selectively targeting a therapeutic agent to activated endothelium expressing E-selectin, comprising administering to a patient a pharmaceutical composition comprising a therapeutically effective amount of an immunoconjugate comprising monoclonal antibody H18/7, or a fragment of said antibody which binds to E-selectin, conjugated to a therapeutic agent, and a pharmaceutically acceptable carrier.

2. The method of claim 1, wherein said therapeutic agent is an anti-thrombotic agent, thrombolytic agent, anti-inflammatory agent, antioxidant, anti-tumor agent, anti-smooth muscle cell proliferative agent, anti-complement agent, immunosuppressive agent, or anti-microbial agent.

3. The method of claim 2, wherein said anti-thrombotic agent is hirudin.

4. An immunoconjugate comprising a monoclonal antibody H18/7, or a fragment of said antibody which binds to E-selectin, conjugated to a therapeutic agent.

5. The immunoconjugate of claim 4, wherein said therapeutic agent is an anti-thrombotic agent, thrombolytic agent, anti-inflammatory agent, antioxidant, anti-tumor agent, anti-smooth muscle cell proliferate agent, anti-complement agent, immunosuppressive agent, or anti-microbial agent.

6. The immunoconjugate of claim 5, wherein said anti-thrombotic agent is hirudin.

7. A method for the treatment of inflammation, comprising administering to a patient a pharmaceutical composition comprising a therapeutically effective amount of an immunoconjugate comprising monoclonal antibody H18/7, or a fragment of said antibody which binds to E-selectin, conjugated to an anti-inflammatory agent, and a pharmaceutically acceptable carrier.

8. A method for the treatment of a microbial infection, comprising administering to a patient a pharmaceutical composition comprising a therapeutically effective amount of an immunoconjugate comprising monoclonal antibody H18/7, or a fragment of said antibody which binds to E-selectin, conjugated to an anti-microbial agent, and a pharmaceutically acceptable carrier.

9. A method for the treatment of post-reperfusion injury, comprising administering to a patient a pharmaceutical composition comprising a therapeutically effective amount of an immunoconjugate comprising monoclonal antibody H18/7, or a fragment of said antibody which binds to E-selectin, conjugated to an anti-thrombotic agent, antioxidant, anti-complement agent, or anti-inflammatory agent, and a pharmaceutically acceptable carrier.

10. A method for the treatment of a malignant tumor, comprising administering to a patient a pharmaceutical composition comprising a therapeutically effective amount of an immunoconjugate comprising monoclonal antibody H18/7, or a fragment of said antibody which binds to E-selectin, conjugated to an anti-tumor agent, and a pharmaceutically acceptable carrier.

11. A method for the treatment of vasculitis, comprising administering to a patient a pharmaceutical composition comprising a therapeutically effective amount of an immunoconjugate comprising monoclonal antibody H18/7, or a fragment of said antibody which binds to E-selectin, conjugated to an anti-inflammatory agent, anti-thrombotic agent, anti-thrombolytic agent, or anti-complement agent, and a pharmaceutically acceptable carrier.

12. A method for the treatment of a vascular smooth muscle cell proliferative disorder, comprising administering to a patient a pharmaceutical composition comprising a therapeutically effective amount of an immunoconjugate comprising monoclonal antibody H18/7, or a fragment of said antibody which binds to E-selectin, conjugated to an anti-smooth muscle cell proliferative agent, and a pharmaceutically acceptable carrier.

13. The method of claim 12, wherein said anti-smooth muscle cell proliferative agent is an anti-thrombin agent.

14. The method of claim 13, wherein said anti-thrombin agent is hirudin.

15. A method for the treatment of acute or chronic allograft rejection, comprising administering to a patient a pharmaceutical composition comprising a therapeutically effective amount of an immunoconjugate comprising monoclonal antibody H18/7, or a fragment of said antibody which binds to E-selectin, conjugated to an anti-inflammatory agent, anti-thrombotic agent, anti-complement agent, or immunosuppressive agent, and a pharmaceutically acceptable carrier.

* * * * *

UNITED STATES PATENT AND TRADEMARK OFFICE
CERTIFICATE OF CORRECTION

PATENT NO. : 5,632,991

DATED : May 27, 1997

INVENTOR(S): Gimbrone, Jr.

It is certified that an error appears in the above-identified patent and that said Letters Patent is hereby corrected as shown below.

Title Page:

On page 3, left column, in the citation beginning with "Polte *et al.*", replace "Leukocyte" with --leukocyte--.

In column 1, line 42, replace "intimation" with --inflammation--.

In column 3, line 3, after "49-61", insert a --)--.

In column 17, line 13, replace "$^{67}Ca$" with --$^{67}Ga$--.

In column 20, line 42, replace "SEQ D" with --SEQ ID--.

Signed and Sealed this

Twentieth Day of January, 1998

BRUCE LEHMAN

Attest:

Attesting Officer

Commissioner of Patents and Trademarks

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 3854 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
CCTGAGACAG  AGGCAGCAGT  GATACCCACC  TGAGAGATCC  TGTGTTTGAA  CAACTGCTTC    60

CCAAAACGGA  AAGTATTTCA  AGCCTAAACC  TTTGGGTGAA  AAGAACTCTT  GAAGTCATGA   120

TTGCTTCACA  GTTTCTCTCA  GCTCTCACTT  TGGTGCTTCT  CATTAAAGAG  AGTGGAGCCT   180

GGTCTTACAA  CACCTCCACG  GAAGCTATGA  CTTATGATGA  GGCCAGTGCT  TATTGTCAGC   240

AAAGGTACAC  ACACCTGGTT  GCAATTCAAA  ACAAAGAAGA  GATTGAGTAC  CTAAACTCCA   300

TATTGAGCTA  TTCACCAAGT  TATTACTGGA  TTGGAATCAG  AAAAGTCAAC  AATGTGTGGG   360

TCTGGGTAGG  AACCCAGAAA  CCTCTGACAG  AAGAAGCCAA  GAACTGGGCT  CCAGGTGAAC   420

CCAACAATAG  GCAAAAAGAT  GAGGACTGCG  TGGAGATCTA  CATCAAGAGA  GAAAAAGATG   480

TGGGCATGTG  GAATGATGAG  AGGTGCAGCA  AGAAGAAGCT  TGCCCTATGC  TACACAGCTG   540
```

```
CCTGTACCAA TACATCCTGC AGTGGCCACG GTGAATGTGT AGAGACCATC AATAATTACA    600
CTTGCAAGTG TGACCCTGGC TTCAGTGGAC TCAAGTGTGA GCAAATTGTG AACTGTACAG    660
CCCTGGAATC CCCTGAGCAT GGAAGCCTGG TTTGCAGTCA CCCACTGGGA AACTTCAGCT    720
ACAATTCTTC CTGCTCTATC AGCTGTGATA GGGGTTACCT GCCAAGCAGC ATGGAGACCA    780
TGCAGTGTAT GTCCTCTGGA GAATGGAGTG CTCCTATTCC AGCCTGCAAT GTGGTTGAGT    840
GTGATGCTGT GACAAATCCA GCCATGGGT TCGTGGAATG TTTCCAAAAC CTGGAAGCT    900
TCCCATGGAA CACAACCTGT ACATTTGACT GTGAAGAAGG ATTTGAACTA ATGGGAGCCC    960
AGAGCCTTCA GTGTACCTCA TCTGGGAATT GGACAACGA GAAGCCAACG TGTAAAGCTG   1020
TGACATGCAG GGCCGTCCGC CAGCCTCAGA ATGGCTCTGT GAGGTGCAGC CATTCCCTG   1080
CTGGAGAGTT CACCTTCAAA TCATCCTGCA ACTTCACCTG TGAGGAAGGC TTCATGTTGC   1140
AGGGACCAGC CCAGGTTGAA TGCACCACTC AAGGGCAGTG ACACAGCAA ATCCAGTTT   1200
GTGAAGCTTT CCAGTGCACA GCCTTGTCCA ACCCCGAGCG AGGCTACATG AATTGTCTTC   1260
CTAGTGCTTC TGGCAGTTTC CGTTATGGGT CCAGCTGTGA GTTCTCCTGT GAGCAGGGTT   1320
TTGTGTTGAA GGGATCCAAA AGGCTCCAAT GTGGCCCCAC AGGGGAGTGG ACAACGAGA   1380
AGCCCACATG TGAAGCTGTG AGATGCGATG CTGTCCACCA GCCCCGAAG GGTTGGTGA   1440
GGTGTGCTCA TTCCCCTATT GGAGAATTCA CCTACAAGTC CTCTTGTGCC TTCAGCTGTG   1500
AGGAGGGATT TGAATTATAT GGATCAACTC AACTTGAGTG CACATCTCAG GGACAATGGA   1560
CAGAAGAGGT TCCTTCCTGC CAAGTGGTAA AATGTTCAAG CCTGGCAGTT CCGGGAAAGA   1620
TCAACATGAG CTGCAGTGGG GAGCCCGTGT TGGCACTGT GTGCAAGTTC GCCTGTCCTG   1680
AAGGATGGAC GCTCAATGGC TCTGCAGCTC GGACATGTGG AGCCACAGGA CACTGGTCTG   1740
GCCTGCTACC TACCTGTGAA GCTCCCACTG AGTCCAACAT TCCCTTGGTA GCTGGACTTT   1800
CTGCTGCTGG ACTCTCCCTC CTGACATTAG CACCATTTCT CCTCTGGCTT CGGAAATGCT   1860
TACGGAAAGC AAAGAAATTT GTTCCTGCCA GCAGCTGCCA AAGCCTTGAA TCAGACGGAA   1920
GCTACCAAAA GCCTTCTTAC ATCCTTTAAG TTCAAAAGAA TCAGAAACAG GTGCATCTGG   1980
GGAACTAGAG GGATACACTG AAGTTAACAG AGACAGATAA CTCTCCTCGG GTCTCTGGCC   2040
CTTCTTGCCT ACTATGCCAG ATGCCTTTAT GGCTGAAACC GCAACACCCA TCACCACTTC   2100
AATAGATCAA AGTCCAGCAG GCAAGGACGG CCTTCAACTG AAAAGACTCA GTGTTCCCTT   2160
TCCTACTCTC AGGATCAAGA AAGTGTTGGC TAATGAAGGG AAAGGATATT TCTTCCAAG   2220
CAAAGGTGAA GAGACCAAGA CTCTGAAATC TCAGAATTCC TTTTCTAACT CTCCCTTGCT   2280
CGCTGTAAAA TCTTGGCACA GAAACACAAT ATTTGTGGC TTTCTTCTT TTGCCCTTCA   2340
CAGTGTTTCG ACAGCTGATT ACACAGTTGC TGTCATAAGA ATGAATAATA ATTATCCAGA   2400
GTTAGAGGA AAAAAATGAC TAAAAATATT ATAACTTAAA AAAATGACAG ATGTTGAATG   2460
CCCACAGGCA AATGCATGGA GGGTTGTTAA TGGTGCAAAT CCTACTGAAT GCTCTGTGCG   2520
AGGGTTACTA TGCACAATTT AATCACTTTC ATCCCTATGG GATTCAGTGC TTCTTAAAGA   2580
GTTCTTAAGG ATTGTGATAT TTTACTTGC ATTGAATATA TTATAATCTT CCATACTTCT   2640
TCATTCAATA CAAGTGTGGT AGGGACTTAA AAAACTTGTA AATGCTGTCA ACTATGATAT   2700
GGTAAAAGTT ACTTATTCTA GATTACCCCC TCATTGTTTA TTAACAAATT ATGTTACATC   2760
TGTTTTAAAT TTATTTCAAA AAGGGAAACT ATTGTCCCCT AGCAAGGCAT GATGTTAACC   2820
AGAATAAAGT TCTGAGTGTT TTACTACAG TTGTTTTTG AAAACATGGT AGAATTGGAG   2880
AGTAAAAACT GAATGGAAGG TTTGTATATT GTCAGATATT TTTCAGAAA TATGTGGTTT   2940
```

-continued

| | | | | | | |
|---|---|---|---|---|---|---|
| CCACGATGAA | AAACTTCCAT | GAGGCCAAAC | GTTTTGAACT | AATAAAAGCA | TAAATGCAAA | 3000 |
| CACACAAAGG | TATAATTTTA | TGAATGTCTT | TGTTGGAAAA | GAATACAGAA | AGATGGATGT | 3060 |
| GCTTTGCATT | CCTACAAAGA | TGTTTGTCAG | ATGTGATATG | TAAACATAAT | TCTTGTATAT | 3120 |
| TATGGAAGAT | TTTAAATTCA | CAATAGAAAC | TCACCATGTA | AAAGAGTCAT | CTGGTAGATT | 3180 |
| TTTAACGAAT | GAAGATGTCT | AATAGTTATT | CCCTATTTGT | TTTCTTCTGT | ATGTTAGGGT | 3240 |
| GCTCTGGAAG | AGAGGAATGC | CTGTGTGAGC | AAGCATTTAT | GTTTATTTAT | AAGCAGATTT | 3300 |
| AACAATTCCA | AAGGAATCTC | CAGTTTTCAG | TTGATCACTG | GCAATGAAAA | ATTCTCAGTC | 3360 |
| AGTAATTGCC | AAAGCTGCTC | TAGCCTTGAG | GAGTGTGAGA | ATCAAAACTC | TCCTACACTT | 3420 |
| CCATTAACTT | AGCATGTGTT | GAAAAAAAA | GTTTCAGAGA | AGTTCTGGCT | GAACACTGGC | 3480 |
| AACGACAAAG | CCAACAGTCA | AAACAGAGAT | GTGATAAGGA | TCAGAACAGC | AGAGGTTCTT | 3540 |
| TTAAGGGGC | AGAAAAACTC | TGGGAAATAA | GAGAGAACAA | CTACTGTGAT | CAGGCTATGT | 3600 |
| ATGGAATACA | GTGTTATTTT | CTTTGAAATT | GTTAAGTGT | TGTAAATATT | TATGTAAACT | 3660 |
| GCATTAGAAA | TTAGCTGTGT | GAAATACCAG | TGTGGTTTGT | GTTTGAGTTT | TATTGAGAAT | 3720 |
| TTTAAATTAT | AACTTAAAAT | ATTTTATAAT | TTTTAAAGTA | TATATTTATT | TAAGCTTATG | 3780 |
| TCAGACCTAT | TTGACATAAC | ACTATAAAGG | TTGACAATAA | ATGTGCTTAT | GTTTAAAAAA | 3840 |
| AAAAAAAAA | AAAA | | | | | 3854 |

( 2 ) INFORMATION FOR SEQ ID NO:2:

( i ) SEQUENCE CHARACTERISTICS:
    ( A ) LENGTH: 1833 base pairs
    ( B ) TYPE: nucleic acid
    ( C ) STRANDEDNESS: single
    ( D ) TOPOLOGY: linear ( i x ) FEATURE:
    ( A ) NAME/KEY: nucleic acid
    ( B ) LOCATION: 1-1833
    ( C ) OTHER INFORMATION:/ label =nucleic acid
        / note = SEQ ID NO:2 begins at base pair position 117 and
        ends at base pair position 1949.

( x i ) SEQUENCE DESCRIPTION: SEQ ID NO:2:

| | | | | | | |
|---|---|---|---|---|---|---|
| ATGATTGCTT | CACAGTTTCT | CTCAGCTCTC | ACTTTGGTGC | TTCTCATTAA | AGAGAGTGGA | 60 |
| GCCTGGTCTT | ACAACACCTC | CACGGAAGCT | ATGACTTATG | ATGAGGCCAG | TGCTTATTGT | 120 |
| CAGCAAAGGT | ACACACACCT | GGTTGCAATT | CAAAACAAAG | AAGAGATTGA | GTACCTAAAC | 180 |
| TCCATATTGA | GCTATTCACC | AAGTTATTAC | TGGATTGGAA | TCAGAAAAGT | CAACAATGTG | 240 |
| TGGGTCTGGG | TAGGAACCCA | GAAACCTCTG | ACAGAAGAAG | CCAAGAACTG | GCTCCAGGT | 300 |
| GAACCCAACA | ATAGGCAAAA | AGATGAGGAC | TGCGTGGAGA | TCTACATCAA | GAGAGAAAAA | 360 |
| GATGTGGGCA | TGTGGAATGA | TGAGAGGTGC | AGCAAGAAGA | AGCTTGCCCT | ATGCTACACA | 420 |
| GCTGCCTGTA | CCAATACATC | CTGCAGTGGC | CACGGTGAAT | GTGTAGAGAC | CATCAATAAT | 480 |
| TACACTTGCA | AGTGTGACCC | TGGCTTCAGT | GGACTCAAGT | GTGAGCAAAT | TGTGAACTGT | 540 |
| ACAGCCCTGG | AATCCCCTGA | GCATGGAAGC | CTGGTTTGCA | GTCACCCACT | GGGAAACTTC | 600 |
| AGCTACAATT | CTTCCTGCTC | TATCAGCTGT | GATAGGGGTT | ACCTGCCAAG | CAGCATGGAG | 660 |
| ACCATGCAGT | GTATGTCCTC | TGGAGAATGG | AGTGCTCCTA | TTCCAGCCTG | CAATGTGGTT | 720 |
| GAGTGTGATG | CTGTGACAAA | TCCAGCCAAT | GGGTTCGTGG | AATGTTTCCA | AAACCCTGGA | 780 |
| AGCTTCCCAT | GGAACACAAC | CTGTACATTT | GACTGTGAAG | AAGGATTTGA | ACTAATGGGA | 840 |
| GCCCAGAGCC | TTCAGTGTAC | CTCATCTGGG | AATTGGGACA | ACGAGAAGCC | AACGTGTAAA | 900 |

```
GCTGTGACAT  GCAGGGCCGT  CCGCCAGCCT  CAGAATGGCT  CTGTGAGGTG  CAGCCATTCC        960
CCTGCTGGAG  AGTTCACCTT  CAAATCATCC  TGCAACTTCA  CCTGTGAGGA  AGGCTTCATG       1020
TTGCAGGGAC  CAGCCCAGGT  TGAATGCACC  ACTCAAGGGC  AGTGGACACA  GCAAATCCCA       1080
GTTTGTGAAG  CTTTCCAGTG  CACAGCCTTG  TCCAACCCCG  AGCGAGGCTA  CATGAATTGT       1140
CTTCCTAGTG  CTTCTGGCAG  TTTCCGTTAT  GGGTCCAGCT  GTGAGTTCTC  CTGTGAGCAG       1200
GGTTTTGTGT  TGAAGGGATC  CAAAAGGCTC  CAATGTGGCC  CCACAGGGGA  GTGGGACAAC       1260
GAGAAGCCCA  CATGTGAAGC  TGTGAGATGC  GATGCTGTCC  ACCAGCCCCC  GAAGGGTTTG       1320
GTGAGGTGTG  CTCATTCCCC  TATTGGAGAA  TTCACCTACA  AGTCCTCTTG  TGCCTTCAGC       1380
TGTGAGGAGG  GATTTGAATT  ATATGGATCA  ACTCAACTTG  AGTGCACATC  TCAGGGACAA       1440
TGGACAGAAG  AGGTTCCTTC  CTGCCAAGTG  GTAAAATGTT  CAAGCCTGGC  AGTTCCGGGA       1500
AAGATCAACA  TGAGCTGCAG  TGGGGAGCCC  GTGTTTGGCA  CTGTGTGCAA  GTTCGCCTGT       1560
CCTGAAGGAT  GGACGCTCAA  TGGCTCTGCA  GCTCGGACAT  GTGGAGCCAC  AGGACACTGG       1620
TCTGGCCTGC  TACCTACCTG  TGAAGCTCCC  ACTGAGTCCA  ACATTCCCTT  GGTAGCTGGA       1680
CTTTCTGCTG  CTGGACTCTC  CCTCCTGACA  TTAGCACCAT  TTCTCCTCTG  GCTTCGGAAA       1740
TGCTTACGGA  AAGCAAAGAA  ATTTGTTCCT  GCCAGCAGCT  GCCAAAGCCT  TGAATCAGAC       1800
GGAAGCTACC  AAAAGCCTTC  TTACATCCTT  TAA                                      1833
```

( 2 ) INFORMATION FOR SEQ ID NO:3:

( i ) SEQUENCE CHARACTERISTICS:
    ( A ) LENGTH: 610 amino acids
    ( B ) TYPE: amino acid
    ( D ) TOPOLOGY: linear ( x i ) SEQUENCE DESCRIPTION: SEQ ID NO:3:

```
Met  Ile  Ala  Ser  Gln  Phe  Leu  Ser  Ala  Leu  Thr  Leu  Val  Leu  Leu  Ile
  1              5                   10                  15

Lys  Glu  Ser  Gly  Ala  Trp  Ser  Tyr  Asn  Thr  Ser  Thr  Glu  Ala  Met  Thr
             20                  25                  30

Tyr  Asp  Glu  Ala  Ser  Ala  Tyr  Cys  Gln  Gln  Arg  Tyr  Thr  His  Leu  Val
         35                  40                  45

Ala  Ile  Gln  Asn  Lys  Glu  Glu  Ile  Glu  Tyr  Leu  Asn  Ser  Ile  Leu  Ser
     50                  55                  60

Tyr  Ser  Pro  Ser  Tyr  Tyr  Trp  Ile  Gly  Ile  Arg  Lys  Val  Asn  Asn  Val
 65                  70                  75                              80

Trp  Val  Trp  Val  Gly  Thr  Gln  Lys  Pro  Leu  Thr  Glu  Glu  Ala  Lys  Asn
                 85                  90                  95

Trp  Ala  Pro  Gly  Glu  Pro  Asn  Asn  Arg  Gln  Lys  Asp  Glu  Asp  Cys  Val
                100                 105                 110

Glu  Ile  Tyr  Ile  Lys  Arg  Glu  Lys  Asp  Val  Gly  Met  Trp  Asn  Asp  Glu
            115                 120                 125

Arg  Cys  Ser  Lys  Lys  Lys  Leu  Ala  Leu  Cys  Tyr  Thr  Ala  Ala  Cys  Thr
        130                 135                 140

Asn  Thr  Ser  Cys  Ser  Gly  His  Gly  Glu  Cys  Val  Glu  Thr  Ile  Asn  Asn
145                 150                 155                             160

Tyr  Thr  Cys  Lys  Cys  Asp  Pro  Gly  Phe  Ser  Gly  Leu  Lys  Cys  Glu  Gln
                165                 170                 175

Ile  Val  Asn  Cys  Thr  Ala  Leu  Glu  Ser  Pro  Glu  His  Gly  Ser  Leu  Val
                180                 185                 190

Cys  Ser  His  Pro  Leu  Gly  Asn  Phe  Ser  Tyr  Asn  Ser  Ser  Cys  Ser  Ile
```

-continued

|  |  | 195 |  |  |  |  | 200 |  |  |  |  | 205 |  |  |
|---|---|---|---|---|---|---|---|---|---|---|---|---|---|---|
| Ser | Cys 210 | Asp | Arg | Gly | Tyr | Leu 215 | Pro | Ser | Ser | Met | Glu 220 | Thr | Met | Gln Cys |
| Met 225 | Ser | Ser | Gly | Glu | Trp 230 | Ser | Ala | Pro | Ile | Pro 235 | Ala | Cys | Asn | Val Val 240 |
| Glu | Cys | Asp | Ala | Val 245 | Thr | Asn | Pro | Ala | Asn 250 | Gly | Phe | Val | Glu | Cys 255 Phe |
| Gln | Asn | Pro | Gly 260 | Ser | Phe | Pro | Trp | Asn 265 | Thr | Thr | Cys | Thr | Phe 270 | Asp Cys |
| Glu | Glu | Gly 275 | Phe | Glu | Leu | Met | Gly 280 | Ala | Gln | Ser | Leu | Gln 285 | Cys | Thr Ser |
| Ser | Gly 290 | Asn | Trp | Asp | Asn | Glu 295 | Lys | Pro | Thr | Cys | Lys 300 | Ala | Val | Thr Cys |
| Arg 305 | Ala | Val | Arg | Gln | Pro 310 | Gln | Asn | Gly | Ser | Val 315 | Arg | Cys | Ser | His Ser 320 |
| Pro | Ala | Gly | Glu | Phe 325 | Thr | Phe | Lys | Ser | Ser 330 | Cys | Asn | Phe | Thr | Cys 335 Glu |
| Glu | Gly | Phe | Met 340 | Leu | Gln | Gly | Pro | Ala 345 | Gln | Val | Glu | Cys | Thr 350 | Thr Gln |
| Gly | Gln | Trp 355 | Thr | Gln | Gln | Ile | Pro 360 | Val | Cys | Glu | Ala | Phe 365 | Gln | Cys Thr |
| Ala | Leu 370 | Ser | Asn | Pro | Glu | Arg 375 | Gly | Tyr | Met | Asn | Cys 380 | Leu | Pro | Ser Ala |
| Ser 385 | Gly | Ser | Phe | Arg | Tyr 390 | Gly | Ser | Ser | Cys | Glu 395 | Phe | Ser | Cys | Glu Gln 400 |
| Gly | Phe | Val | Leu | Lys 405 | Gly | Ser | Lys | Arg | Leu 410 | Gln | Cys | Gly | Pro | Thr 415 Gly |
| Glu | Trp | Asp | Asn 420 | Glu | Lys | Pro | Thr | Cys 425 | Glu | Ala | Val | Arg | Cys 430 | Asp Ala |
| Val | His | Gln 435 | Pro | Pro | Lys | Gly | Leu 440 | Val | Arg | Cys | Ala | His 445 | Ser | Pro Ile |
| Gly | Glu 450 | Phe | Thr | Tyr | Lys | Ser 455 | Ser | Cys | Ala | Phe | Ser 460 | Cys | Glu | Glu Gly |
| Phe 465 | Glu | Leu | Tyr | Gly | Ser 470 | Thr | Gln | Leu | Glu | Cys 475 | Thr | Ser | Gln | Gly Gln 480 |
| Trp | Thr | Glu | Glu | Val 485 | Pro | Ser | Cys | Gln | Val 490 | Val | Lys | Cys | Ser | Ser 495 Leu |
| Ala | Val | Pro | Gly 500 | Lys | Ile | Asn | Met | Ser 505 | Cys | Ser | Gly | Glu | Pro 510 | Val Phe |
| Gly | Thr | Val 515 | Cys | Lys | Phe | Ala | Cys 520 | Pro | Glu | Gly | Trp | Thr 525 | Leu | Asn Gly |
| Ser | Ala 530 | Ala | Arg | Thr | Cys | Gly 535 | Ala | Thr | Gly | His | Trp 540 | Ser | Gly | Leu Leu |
| Pro 545 | Thr | Cys | Glu | Ala | Pro 550 | Thr | Glu | Ser | Asn | Ile 555 | Pro | Leu | Val | Ala Gly 560 |
| Leu | Ser | Ala | Ala | Gly 565 | Leu | Ser | Leu | Leu | Thr 570 | Leu | Ala | Pro | Phe | Leu 575 Leu |
| Trp | Leu | Arg | Lys 580 | Cys | Leu | Arg | Lys | Ala 585 | Lys | Lys | Phe | Val | Pro 590 | Ala Ser |
| Ser | Cys | Gln 595 | Ser | Leu | Glu | Ser | Asp 600 | Gly | Ser | Tyr | Gln | Lys 605 | Pro | Ser Tyr |
| Ile | Leu 610 |  |  |  |  |  |  |  |  |  |  |  |  |  |